(12) United States Patent
Lee

(10) Patent No.: US 10,806,861 B2
(45) Date of Patent: *Oct. 20, 2020

(54) DENTAL SYRINGE WITH STABILIZER FOR REMOVABLE NEEDLE

(71) Applicant: Alexander E. Lee, Closter, NJ (US)

(72) Inventor: Alexander E. Lee, Closter, NJ (US)

(*) Notice: Subject to any disclaimer, the term of this patent is extended or adjusted under 35 U.S.C. 154(b) by 315 days.

This patent is subject to a terminal disclaimer.

(21) Appl. No.: 15/785,442

(22) Filed: Oct. 17, 2017

(65) Prior Publication Data

US 2018/0099096 A1  Apr. 12, 2018

Related U.S. Application Data

(63) Continuation-in-part of application No. 15/688,621, filed on Aug. 28, 2017, now abandoned, which is a
(Continued)

(51) Int. Cl.
*A61M 5/24* (2006.01)
*A61M 5/32* (2006.01)
(Continued)

(52) U.S. Cl.
CPC .......... *A61M 5/24* (2013.01); *A61M 5/31515* (2013.01); *A61M 5/321* (2013.01);
(Continued)

(58) Field of Classification Search
CPC .... A61M 5/32; A61M 5/3202; A61M 5/3216; A61M 5/3213; A61M 5/3269;
(Continued)

(56) References Cited

U.S. PATENT DOCUMENTS 1,012,700 A   12/1910   Payne
1,532,744 A    4/1924   Hein
(Continued)

FOREIGN PATENT DOCUMENTS

EP   0 441 628 A2   8/1991
GB   2 496 858 A    5/2013

OTHER PUBLICATIONS

International Search Report in PCT/US16/18587, dated Apr. 29, 2016.
(Continued)

*Primary Examiner* — Lauren P Farrar
(74) *Attorney, Agent, or Firm* — Collard & Roe, P.C.

(57) ABSTRACT

A needle assembly (14), for use with a syringe (3) and a medicine cartridge (12); has a molded body (14B). A needle (14A) is housed in, affixed to, and reinforced by the molded body (14B). The needle (14A) has a single tube which includes a tip (311), and a tip-ward needle (31) extending ring-ward from said tip into the molded body (14B). The tip-ward needle becomes a cartridge needle (531) within the molded body (14B). The cartridge needle (531) extends tip-ward from the molded body (14B). The molded body (14B), is molded as a single structure, and includes: a domed cylinder (248), at the molded body (14B)'s tip-ward end; a flange (22) ringward of the molded body (14B); and fins (251). The fins are molded radially from the domed cylinder (248). The fins are vertically molded from the flange (22); and reinforce the fins to the flange. A second cylinder (244), is extended ringward from the flange (22). A conical portion (15) is molded ringward from the second cylinder (244). The cone flares out ring-ward to a widest part (631) of the conical portion (15), at a ringward end (500) of the molded body to an annular surface (510) at the widest part (631) of the conical portion (15). The cartridge needle (531) has a molded support located tip-ward of the annular surface
(Continued)

(510). A needle shaft (514) is at a central longitudinal axis of the molded body (14B). The needle (14A) passes through needle shaft.

16 Claims, 34 Drawing Sheets

Related U.S. Application Data continuation-in-part of application No. 15/552,493, filed on Aug. 21, 2017, which is a continuation-in-part of application No. PCT/US2016/018587, filed on Feb. 19, 2016.

(60) Provisional application No. 62/118,310, filed on Feb. 19, 2015.

(51) Int. Cl.
*A61M 5/315* (2006.01)
*A61M 5/34* (2006.01)

(52) U.S. Cl.
CPC .......... *A61M 5/3205* (2013.01); *A61M 5/346* (2013.01); *A61M 2005/2414* (2013.01)

(58) Field of Classification Search
CPC .. A61M 5/002; A61M 5/31515; A61M 5/346; A61M 5/24; A61M 2005/2488; A61M 2210/0625; A61M 2005/2414
See application file for complete search history.

(56) References Cited

U.S. PATENT DOCUMENTS

| | | | |
|---|---|---|---|
| 2,147,616 A | | 2/1939 | Chaput |
| 2,169,371 A | * | 8/1939 | Payne .................... A61M 5/344 604/242 |
| 2,956,563 A | | 10/1960 | Sarnoff |
| 3,848,593 A | | 11/1974 | Baldwin |
| 4,892,525 A | * | 1/1990 | Hermann, Jr. ......... A61M 5/002 206/365 |
| 4,931,040 A | | 6/1990 | Haber |
| 5,069,225 A | | 12/1991 | Okamura |
| 5,205,827 A | * | 4/1993 | Novacek .................... A61L 2/28 604/110 |
| 5,501,670 A | * | 3/1996 | Sak ..................... A61M 5/31511 604/110 |
| 6,764,471 B2 | | 7/2004 | Lee |
| 8,128,605 B2 | | 3/2012 | Masi et al. |
| 2002/0004647 A1 | * | 1/2002 | Leong .................. A61B 5/1545 604/168.01 |
| 2011/0068034 A1 | | 3/2011 | Hwang et al. |

OTHER PUBLICATIONS

European Office Action in EP 16753107.8-1122, dated Feb. 12, 2019.
By Wilburia Q. Lindh, Marilyn Pooler, Carol D. Iamparo, Barbara M. Dahl; Combination Disposable/Nondisposable Cartridge Injection Systems; 5th ed., 2014, p. 792, Fig. 24-10, "The Carpuject is a type of cartridge-injection system with a click-lock mechanism for safety." book: Delmar's Clinical Medical Assisting, isbn= 1133603408, Publisher: Delmar, Steven Helba, Clifton Park, NY, US, 2013.
YAGME12, Carpuject, https://www.youtube.com/watch?v=ICJYr-0VIrA YouTube video, & Screen-grabs from said video, publisher: yagme12, Published on Apr 1, 2014, city and/or country where published: unknown.
Photo of three Carpuject metal syringes, assembled to screw-on needles. Standardized medicine vials are to be inserted into the syringe bodies. The syringes or similar designs may date to the 1950s.
Carpuject, From Wikipedia, https://en.wikipedia.org/wiki/Carpuject, The Carpuject is a syringe for the administration of injectable fluid. It was patented by the Sterling Drug Company, which became the Sterling Winthrop, after World War II. The Carpuject competed with the Tubex injection system developed by Wyeth. Redesigned several times. In 1988 Kodak purchased Winthrop Labs. 1994 sold to Sanofi, a French pharmaceutical company, now Sanofi Aventis. In 1997 Sanofi sold to Abbott Laboratories. 2004 Abbott separated its hospital supply line: Hospira, May 30, 2017.
Tubex, The Tubex Syringe cartridge developed c. 1943 during World War II by the WYETH company. It is a drug pre-filled glass cartridge syringe with attached sterile needle, which is inserted in a reusable stainless steel holder (now plastic). https://en.wikipedia.org/wiki/Tubex_(syringe_cartridge).

* cited by examiner

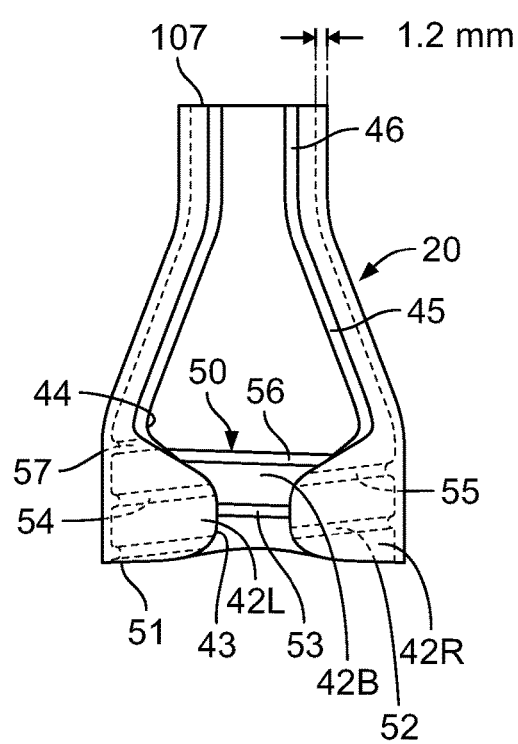
FIG. 4
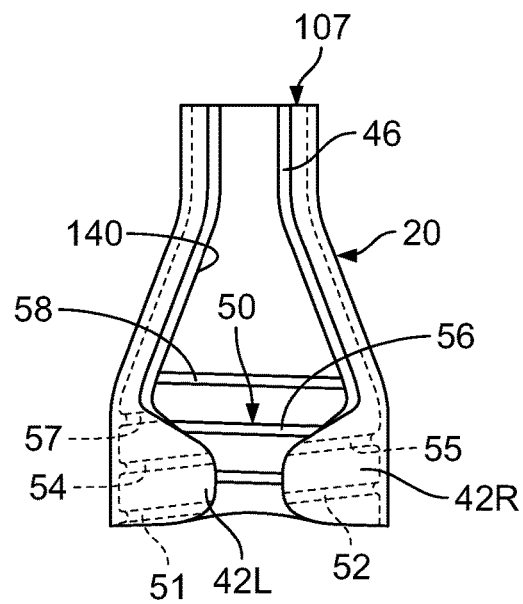
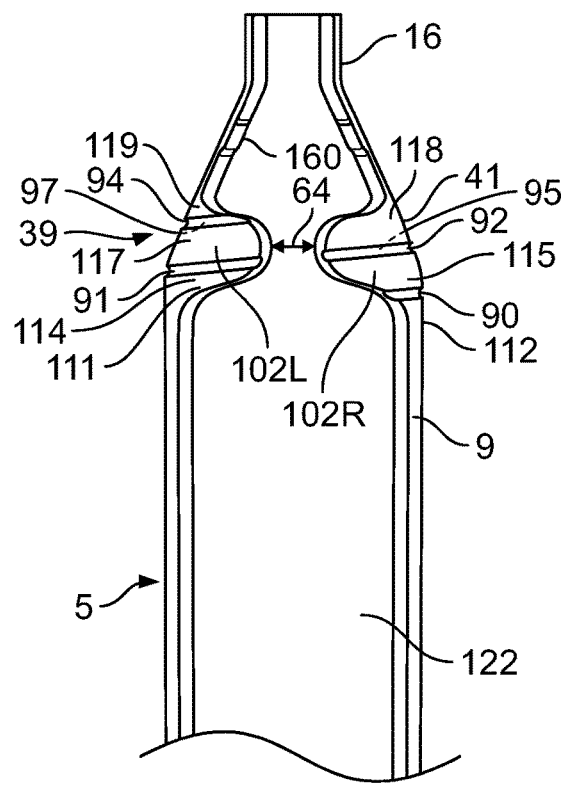
FIG. 5

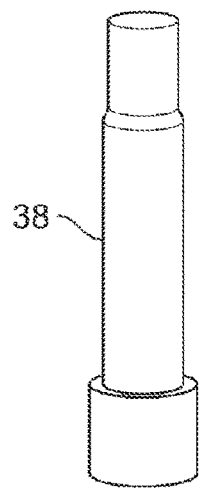
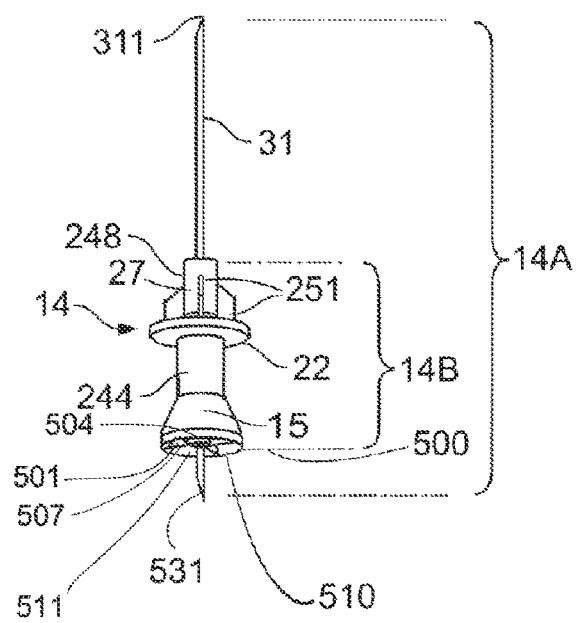
Fig. 47
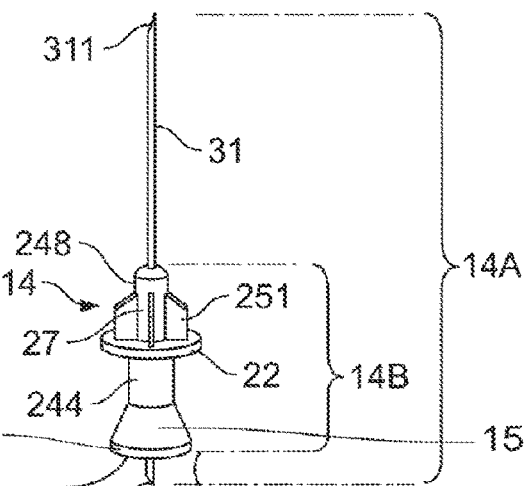
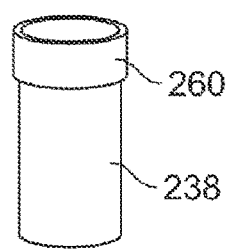
FIG. 46

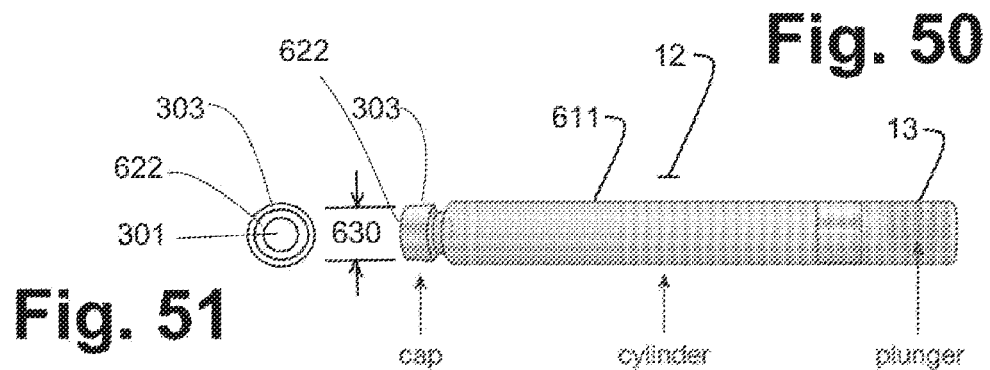
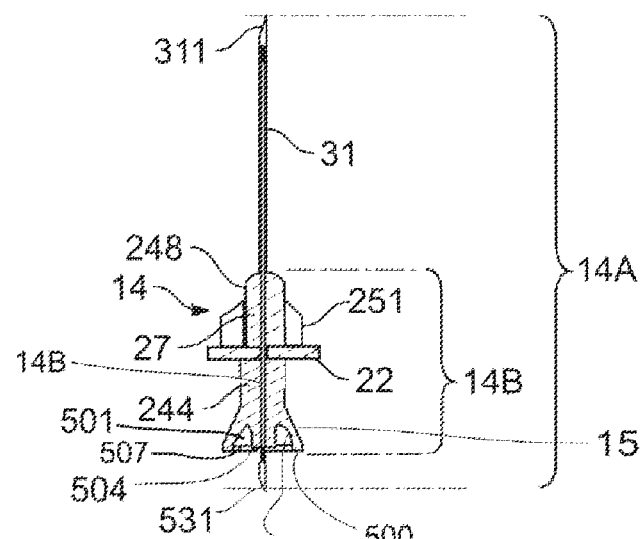
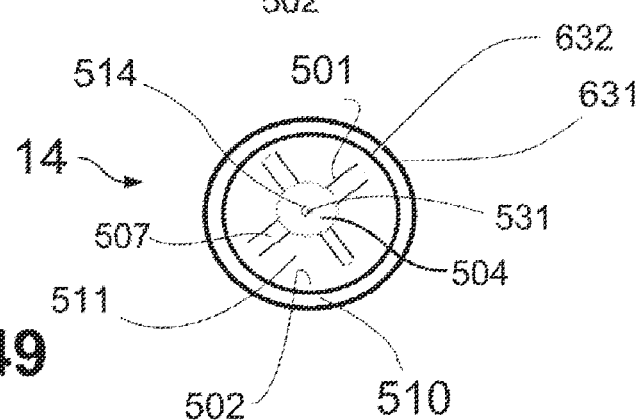

DENTAL SYRINGE WITH STABILIZER FOR REMOVABLE NEEDLE

This application is a Continuation-in-Part Application taking priority and benefit of all common subject matter of:
- U.S. Continuation-in-Part Ser. No. 15/688,621 filed 29 Aug. 2017;
- U.S. Bypass Continuation-in-Part application Ser. No. 15/552,493, filed 21 Aug. 2017; PCT/US16/18587 filed 19 Feb. 2016; and
- U.S. Provisional Patent Application 62/118,310 filed 19 Feb. 2015;

all of which applications are incorporated in this application by reference; and the Inventor's U.S. Pat. No. 6,764,471 B2 Granted: Jul. 20, 2004, on application number: U.S. Ser. No. 10/008,373 is hereby incorporated by reference

FIELD OF THE INVENTION

The present invention relates to a new type of dental syringe system, including a novel needle assembly

DESCRIPTION OF THE RELATED ART

In the dental syringe art, the conventional syringe is adapted to allow the dentist to retract the syringe plunger after the initial stick, in order to ascertain that he has not hit a blood vessel, by using his thumb in the thumb ring of the syringe, pulling back on the plunger and observing the anesthetic vial to determine if blood has been pulled into the syringe. If it has, this indicates that he must find a new spot for the injection point in order to avoid injecting anesthetic into the bloodstream via a blood vessel. There are two reasons for this:
1. The anesthetic usually contains epinephrine, which can affect heart rate adversely.
2. If the anesthetic is taken away from the site by the blood vessel, it will fail to anaesthetize the site.

Thus, in contrast to the usual medical syringe used by doctors, in which the entire syringe is generally disposable, the dental syringe has a reusable metal framework. Medication is usually in a disposable cartridge. So this type of syringe is also known as a cartridge syringe.

BACKGROUND OF THE INVENTION

The closest reference we are aware of in the art is the Present Inventor's earlier patent:
- U.S. Pat. No. 6,764,471 B2, Granted: Jul. 20, 2004, on application number: U.S. Ser. No. 10/008,373
- Filing date Nov. 13, 2001, Priority date Nov. 13, 2000
- Inventor Alexander E. Lee The present invention improves on the disclosure of said present inventor's prior patent.

U.S. Pat. No. 6,764,471 B2 is hereby incorporated by reference.

Other References:
Hospira™ (part of Abbott Labs™) has Carpuject™ syringes.
See: http://en.wikipedia.org/wiki/Carpuject
https://www.youtube.com/watch?v=r4a9E4oV6jY

BRIEF DESCRIPTION

The present invention provides a sheath, which snaps or screws on to threads on the needle-end, or tip, of the syringe to stabilize the needle during injection. This sheath will be made out of either plastic or metal and clipped onto the syringe.

This sheath will allow the insertion of a needle assembly, in the sheath's resting position.

We will define axial directions used in this application as:
Tip-ward=towards the needle tip, sometimes called needle-ward; and
Ring-ward=toward the thumb ring or actuator ring=the opposite direction to tip-ward.

After insertion of the needle, this sheath will be rotated to push the needle assembly tip-ward, thereby seating a conical segment of the needle assembly, against a cooperatively shaped conical part of the interior of the syringe body's tip-ward end.

The sheath will thus stabilize the needle, and thereby facilitate changing anesthetic cartridges during multiple injections.

Further rotation of the sheath will cause the flexible sheath to jump the threads on the syringe and thereby relieve the seating pressure and allow the needle to fall from the syringe into a sharps container.

Alternatively, reversing rotation of the sheath will also relieve the seating pressure and allow the needle to fall from the syringe into a sharps container.

BRIEF DESCRIPTION OF THE DRAWINGS

FIG. 4 is a front elevation of the sheath.

FIG. 5 is an exploded front elevation of the tip-ward end of the syringe, with the sheath shown above the syringe body.

FIG. 46 is a perspective view, from slightly tip-ward, of the alternate embodiment of the needle assembly, with caps exploded to show the needles.

FIG. 47 is a perspective view, from slightly ring-ward, of the alternate embodiment of the protective caps needle assembly.

FIG. 48 is an elevation in section through the center of the alternate embodiment of needle assembly.

FIG. 49 is an enlarged elevation of the ring-ward end of the alternate embodiment of needle assembly.

FIG. 50 is a front elevation of a medicine cartridge.

FIG. 51 is an elevation of the tip-ward surface of the medicine cartridge.

DETAILED DESCRIPTION OF THE DRAWINGS

Figure 1:
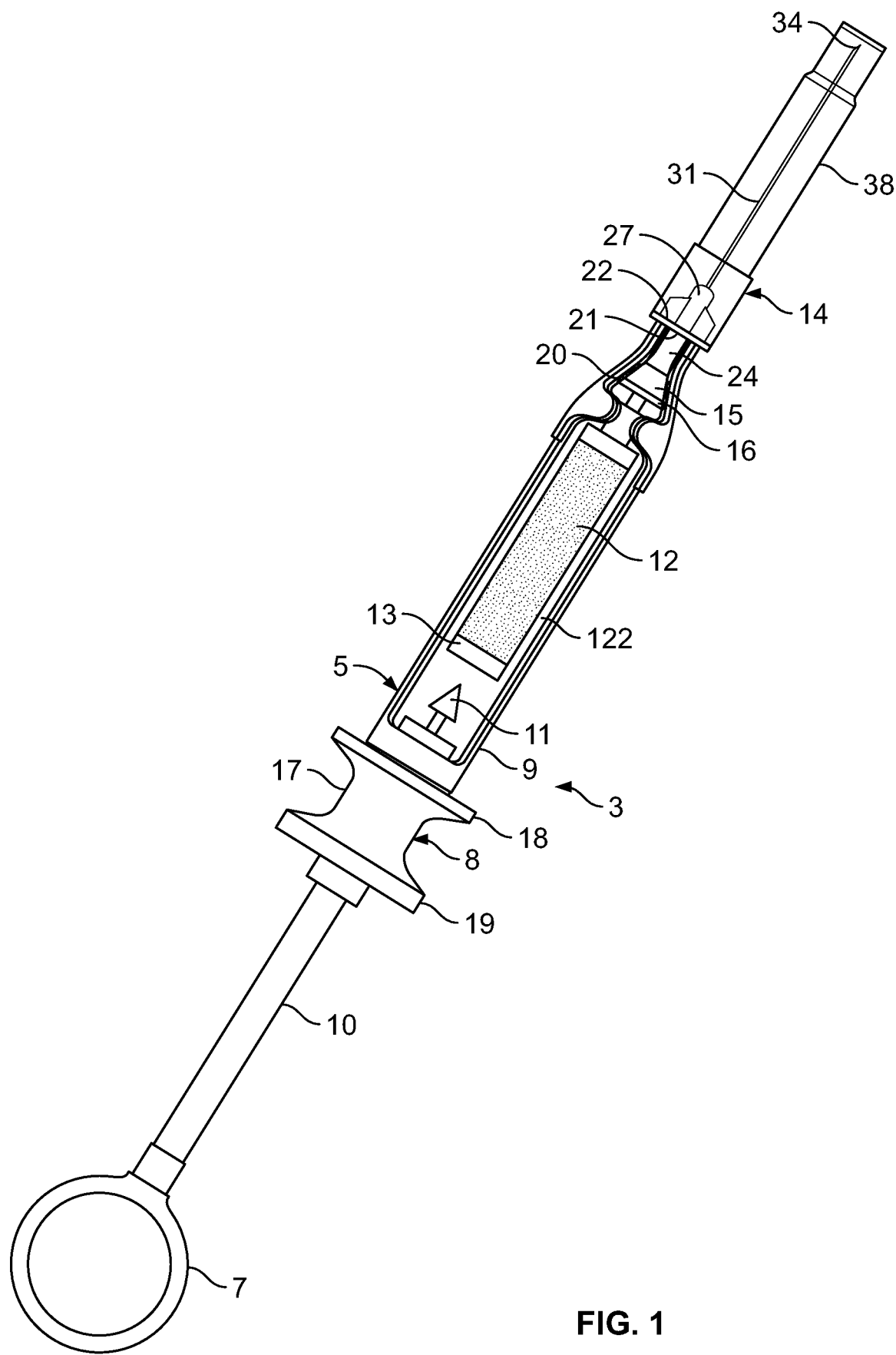
FIG. 1 is a front elevation, of a dental syringe system of the present invention.

FIG. 1 is a front elevation, of the present invention, which provides a dental syringe system. A dental syringe is also known as a cartridge syringe. There are some applications for this syringe and needle system, in the general medical field. If the medications are supplied in the cartridge form rather than a vial or ampule, then this cartridge syringe system can deliver the medications more: easily, simply, and safely.

The prior art requires a user to:
aspirate the medications from the vials and ampules into the medical grade disposable (plastic) syringes, which typically use a large bore needles (20 or 22 gauge); and then inject the medications into a person, The present invention can deliver the medications using the smaller bore needles, if the medications are placed into the cartridge form.

The system, when assembled, forms an assembly which is generally designated 3.

A syringe 5 comprises a thumb ring 7, and a finger grip 8, on a syringe body 9.

I will hereinafter describe and claim the thumb ring 7 as an actuator ring 7, to avoid claiming a human body part, the thumb.

Shaft 10 slidably mounts actuator ring 7 to syringe body 9. At the tip-ward end of shaft 10 is a harpoon 11.

A medicine cartridge 12 is mountable in syringe body 9 of syringe 5. This facilitates use of a narrower gage needle such as 27-gage. Medicine cartridge 12 has a slidable seal 13, into which harpoon 11 can be inserted and anchored to form a plunger (13, 11, 10, & 7) with shaft 10, which can then be slid: tip-ward; or ring-ward; by manipulating the actuator ring 7 in those directions. The ring-ward direction will be referred to in the claims as a ring-ward direction. The actuator ring 7 is configured to be controlled by a thumb, controlling the actuator ring 7 ring-ward to expand or tip-ward contract the volume of the cartridge.

Finger grip 8 comprises a recess 17, and a pair of flanges axial to the recess 17:
tip-ward finger flange 18, and
ring-ward finger flange 19.

But before harpoon 11 is inserted into the cartridge, needle assembly 14 is placed with a conical portion 15, of needle assembly 14, seated inside the matching conical end 16 of syringe body 9. A removable sheath 20 is configured to retain the needle assembly 14 in the syringe body 9.

The syringe body 9 has an external spiral mount 40 on the cylindrical portion of syringe body 9. The external spiral mount 40 includes a threaded matching groove or thread on the outside of the cylindrical portion of syringe body 9.

FIGS. 4 & 5 show the sheath 20 has an internal spiral mount 50, which comprises an internal thread 50, having thread segments: 51, 52, 53, 54, 55, 56, & 57.

The sheath 20 and its internal thread 50 may be rotated in a loosening direction, which would be counter-clockwise when viewed from the tip-ward end. This clockwise rotation causes the tip-ward end 21 of sheath 20 to push against flange 22 on a cylindrical portion 27 of needle assembly 14, and thereby seat conical portion 15 of needle assembly 14 firmly against matching internal, conical end 16 of syringe body 9.

Sheath 20 will be made of a plastic which has a melting temperature above 137 degrees Celsius so that the sheath 20 may be autoclaved. The sheath plastic should also be somewhat elastic (to allow insertion and removal from the syringe), and relatively cheap and easy to manufacture. The presently preferred plastic is nylon. The sheaths 20 are disposable (after multiple uses). New sheaths can be bought separately.

Needle 31 has a point 34.

We define the longitudinal axis 31A for all parts of this application as the axis along which needle 31 is intended to be located when in place.

Figures 20, 20A:
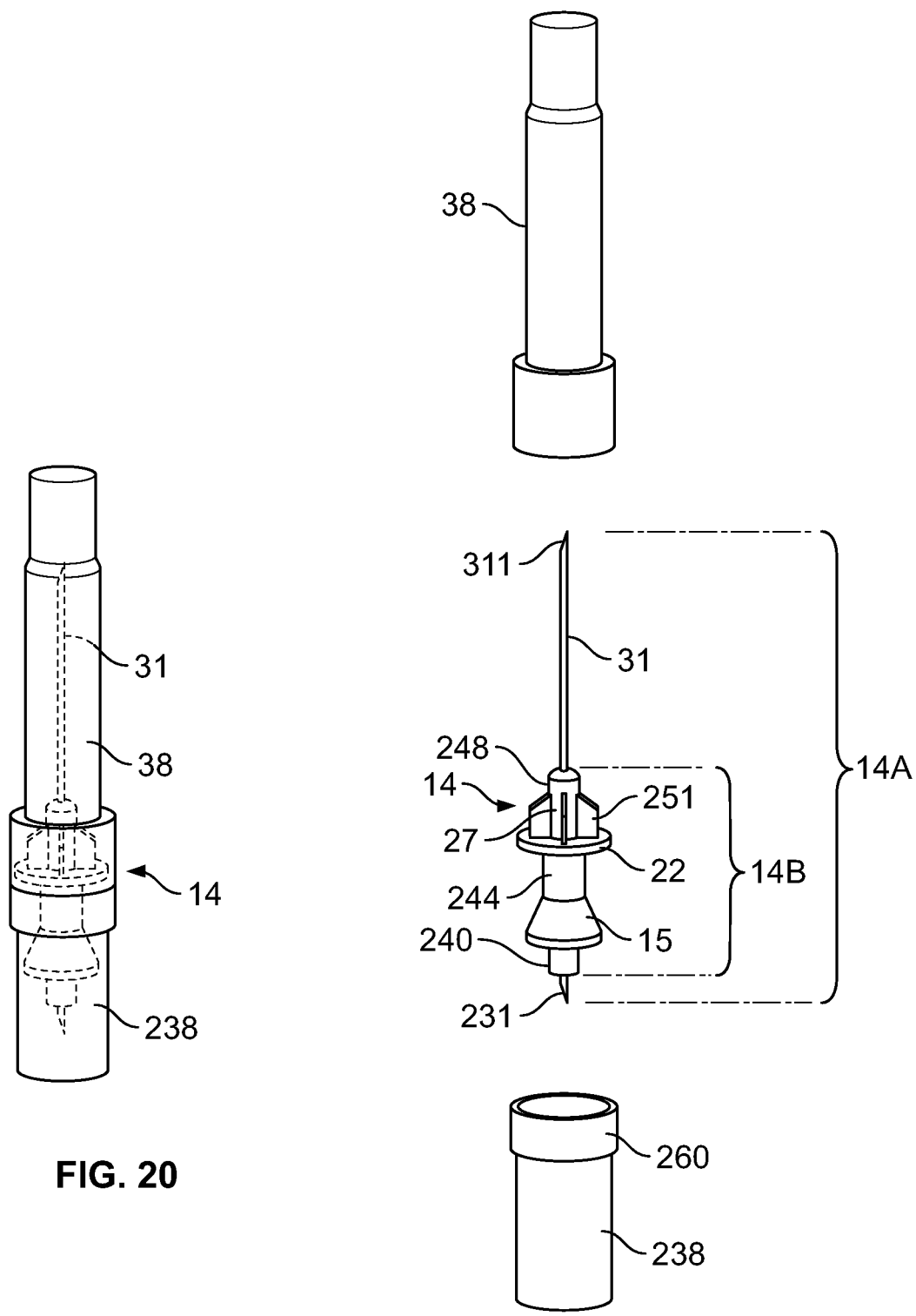
FIG. 20 is a perspective view of the needle assembly.
FIG. 20A is an exploded perspective view of the needle assembly.

FIGS. 20 & 20A show that needle 31 and point 34 are supplied covered by a safety cap 38, protecting a user from the point 34 of needle 31.

Syringe body 9 comprises a spiral groove or grooves 39, in a grooved part 40 of syringe body 9. The groove is preferably on a cylindrical part of an outside surface of the syringe body 9. The groove is spiral.

Figure 9:
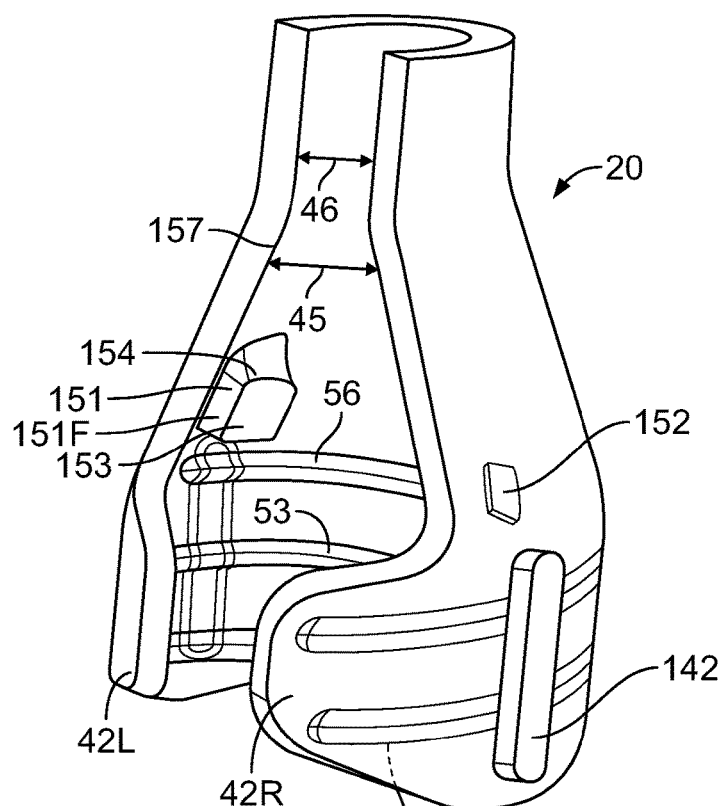
FIG. 9 is a front oblique view of the sheath.

FIGS. 1, 4, 5 & 6, & 10 show front views of sheath 20. Sheath front 42 (FIG. 10) has a left side 42L and right side 42R. Front 42 is open at varying widths at 43-44 (FIG. 10); 45 & 46 (FIG. 9).

Figure 2:
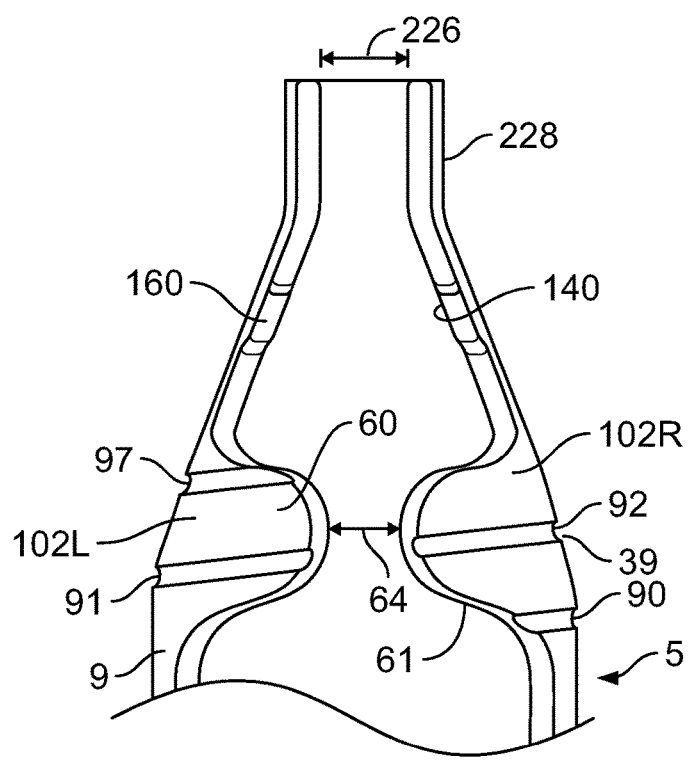
FIG. 2 is a front elevation of part of a syringe of the present invention.
Figure 3:
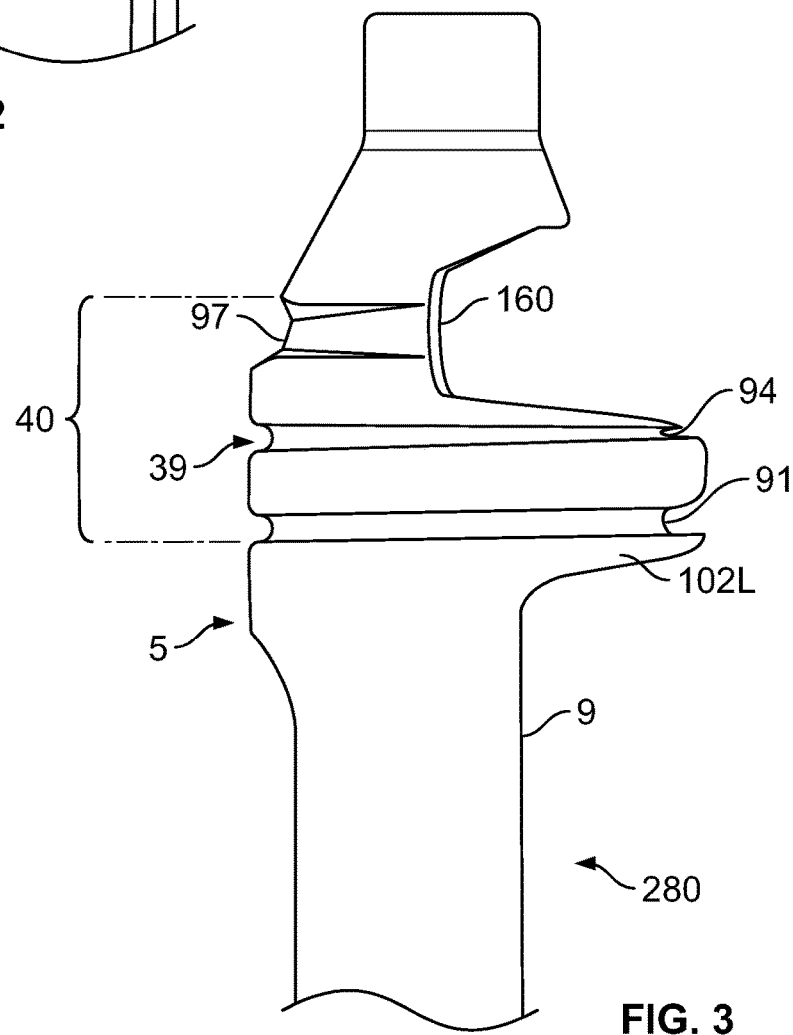
FIG. 3 is a side elevation thereof.

In FIG. 4, internally threaded sheath 20, snaps and/or screws by threads 50, in segments 51-57; on to grooves 39, shown in FIG. 2 front elevation; in FIG. 3 side elevation; and FIG. 5 exploded view.

FIG. 2 is a front elevation of the tip-ward end of the syringe 5 syringe body 9, without the sheath. Syringe front walls 102L & 102R are separated by a front gap 64 to allow the needle assembly 14 to be inserted.

Figure 19:
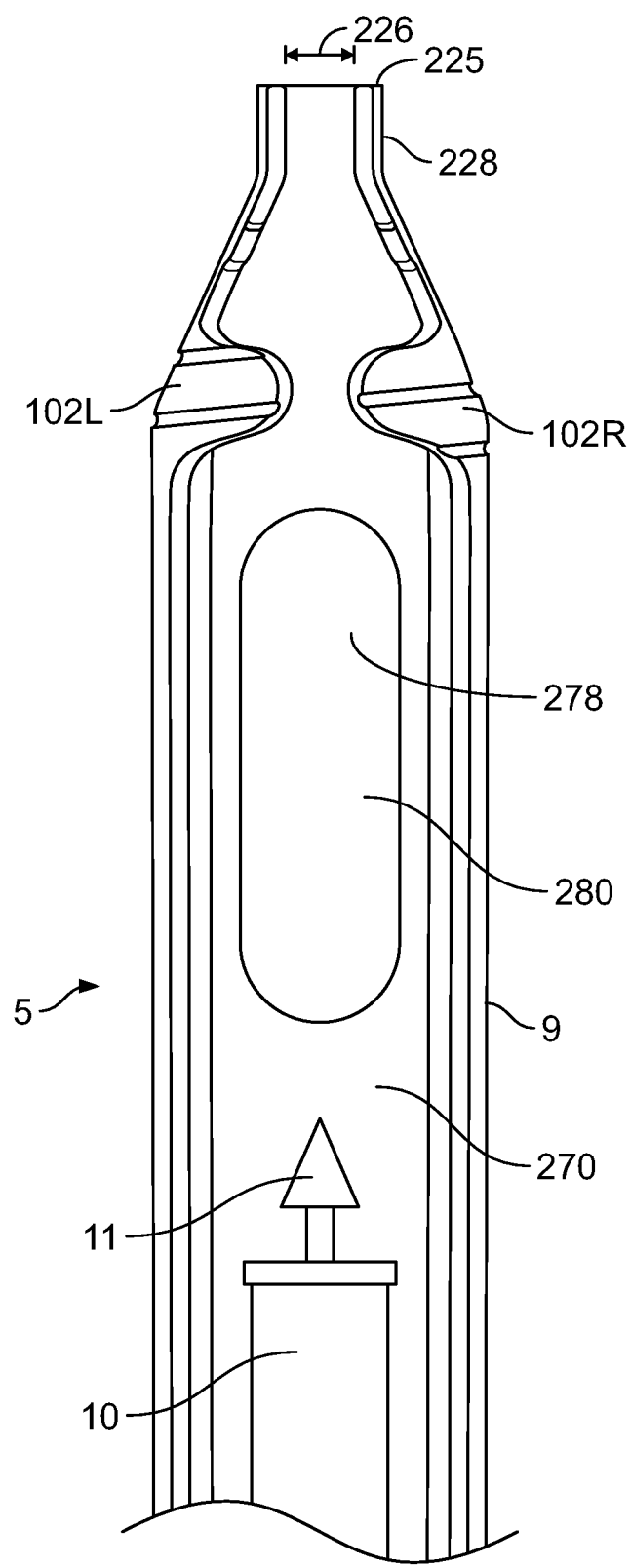
FIG. 19 is a front elevation of said syringe body with the shaft mounted on the body.

In the photos that were FIGS. 2 & 19 of the Provisional Application 62/118,310, a non-functional piece of paper was placed against the back-wall so the front walls 102L & 102R and gap 64 could be seen in FIG. 19 without being confused by back wall reflections of the stainless steel syringe body 9.

FIG. 3 is a side elevation of the tip-ward end of the syringe 5 including syringe body 9, without the sheath. Grooved part 40 comprises groove 39. Groove segments 91-97 are separated by lands 111-119.

FIG. 4 is a front elevation of sheath 20, which sheath 20 will be made out of either plastic or metal and clipped onto the syringe. The presently preferred embodiment is clear nylon with a wall thickness of 1.2 mm. It is softer than the metal syringe, and elastically flexible, so that it springs open and closed a little. The sheath must be autoclavable. The front 42 of sheath 20 is open at gaps of varying widths at 43, 44 (FIG. 10), 45 to 46 (FIG. 9), to allow needle assembly 14 to be inserted into the syringe body 9 from the front.

A protruding thread 50, matches the groove 39 (FIG. 5) on the grooved part 40 of syringe body 9.

As on FIG. 4, thread 50 begins ring-ward at segment 51 on front-wall 42L,
is interrupted at gap 43,
continues at segment 52 continuously around the back-wall 42B as segment 53,
continues continuously as segment 54 around inside the front-wall 42L,
is interrupted at gap 43,
continues at segment 55 continuously inside the front-wall 42R, continuously around the back-wall 42B as segment 56,
continues continuously as segment 57 around inside the front-wall 42R, and
segment 57 ends at the gap at 44, the tip-ward end of thread 50.

FIG. 5 is an exploded view showing the sheath 20 above the syringe 5. There are corresponding groove segments 91, 92, 94, 95, 97 on syringe body 9 which correspond to thread 50.

Sheath 20 should be installed on syringe 5 syringe body 9, first. This can be done by:
  Placing sheath 20 needle ward of conical part 16, and spinning sheath 20 in a tightening direction until thread 50 grabs groove 39 and continuing to tighten, past some stops, until a stop at the position shown in FIGS. 1 & 6.
  Or:
  Placing sheath 20 tip-ward of conical part 16; and pushing ring-ward on tip 107 of sheath 20.

Thread segment 51 rides over land 117, to snap into groove 94 while thread segment 52 rides over land 115, to snap into groove 92.

A further push on tip 107 causes:
thread segment 51 to ride over land 114, to snap into groove 91, while thread segment 52 rides over land 115, to snap into groove 92; while thread segment 54 rides over land 117, to snap into groove 94, while thread segment 55 rides over land 115, to snap into groove 92.

Figure 6:
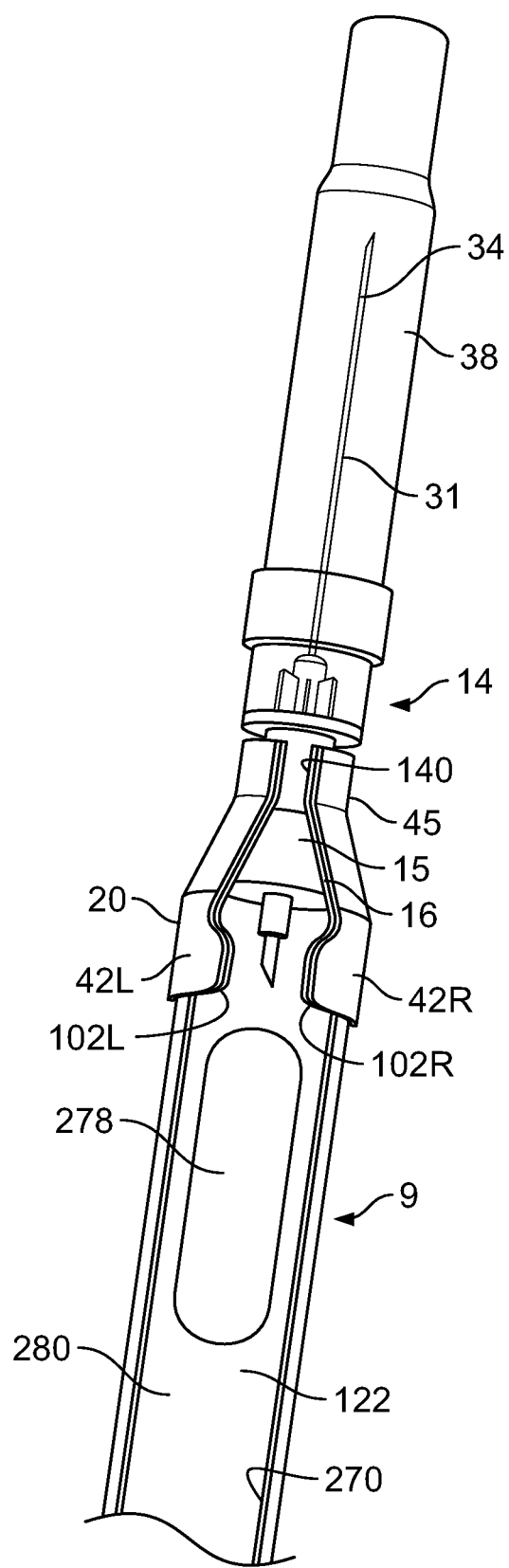
FIG. 6 is a front lower perspective view of the syringe, sheath in position to receive a needle assembly, and a needle assembly.

Sheath 20 is now positioned as shown in FIGS. 1 & 6, ready to receive the needle assembly 14.

This sheath 20 will allow the insertion of a needle assembly 14, in the sheath 20's resting position, shown in FIGS. 1 & 6. The needle assembly 14's conical portion 15 is inserted through gap 45 of sheath 20, to seat against the inside 140 of syringe cone 16.

FIG. 6 is a front elevation of the syringe, with sheath 20 in position to receive a needle assembly 14. The needle assembly 14 has been placed in the syringe, but not yet secured by rotating sheath 20. A cartridge ejection slot 278 is provided.

In FIG. 1, to eject a medicine cartridge 12:
place a finger and thumb at ejection slot 278 and withdraw actuator-ring 7, and harpoon 11 ring-ward;
turn the syringe front-down over a waste container; and push a finger through cartridge ejection slot 278 against the medicine cartridge 12, until the medicine cartridge falls out the long body front opening 122 on the front of syringe body 9 (FIG. 1).

To remove a needle assembly 14, reversing rotation of the sheath 20 will relieve the seating pressure and allow the needle assembly 14 to fall directly from the syringe into a sharps container by inverting the syringe (over the sharps container).

At this point it's useful to fully describe and show the details of the presently preferred sheath 20.

Figure 7:
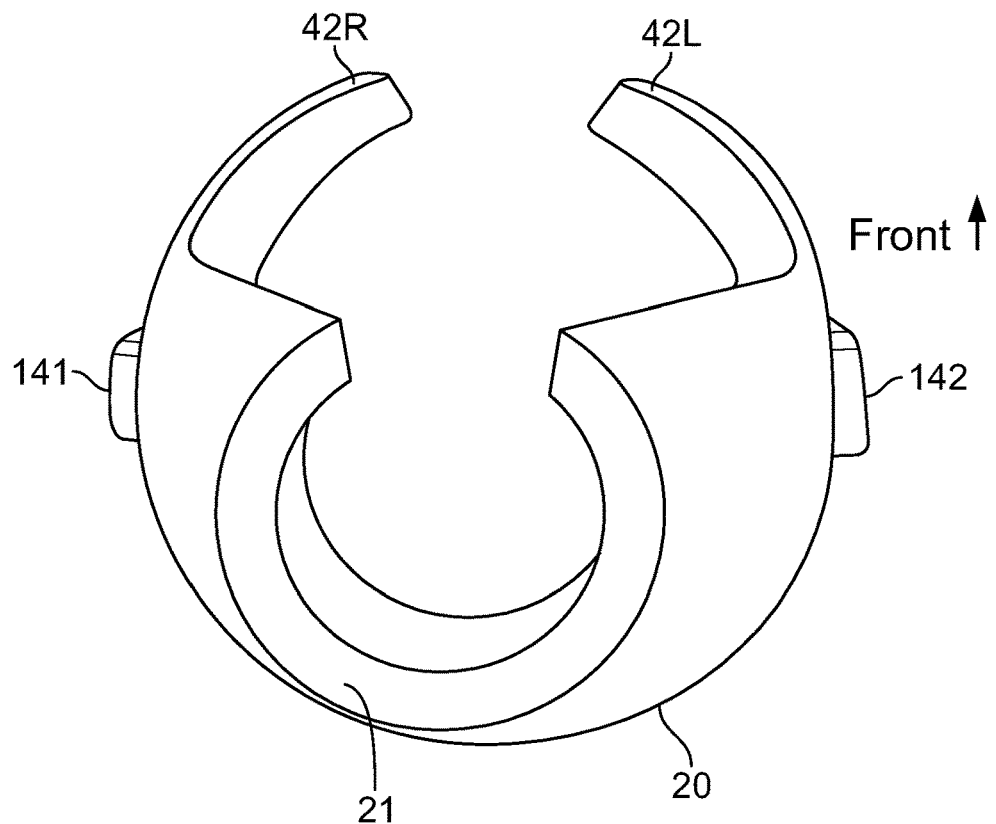
FIG. 7 is a slightly oblique top perspective view of the sheath 20, looking in a thumb-ward direction.

FIG. 7 is a slightly oblique top perspective view of sheath 20, looking in a ring-ward direction. Finger ribs 141 & 142, on the outside of sheath 20, assist the dentist in rotating the sheath by providing grip. Tip-ward end 21 is the surface which pushes against (FIG. 1) flange 22 on a cylindrical portion 27 of needle assembly 14.

Figure 8:
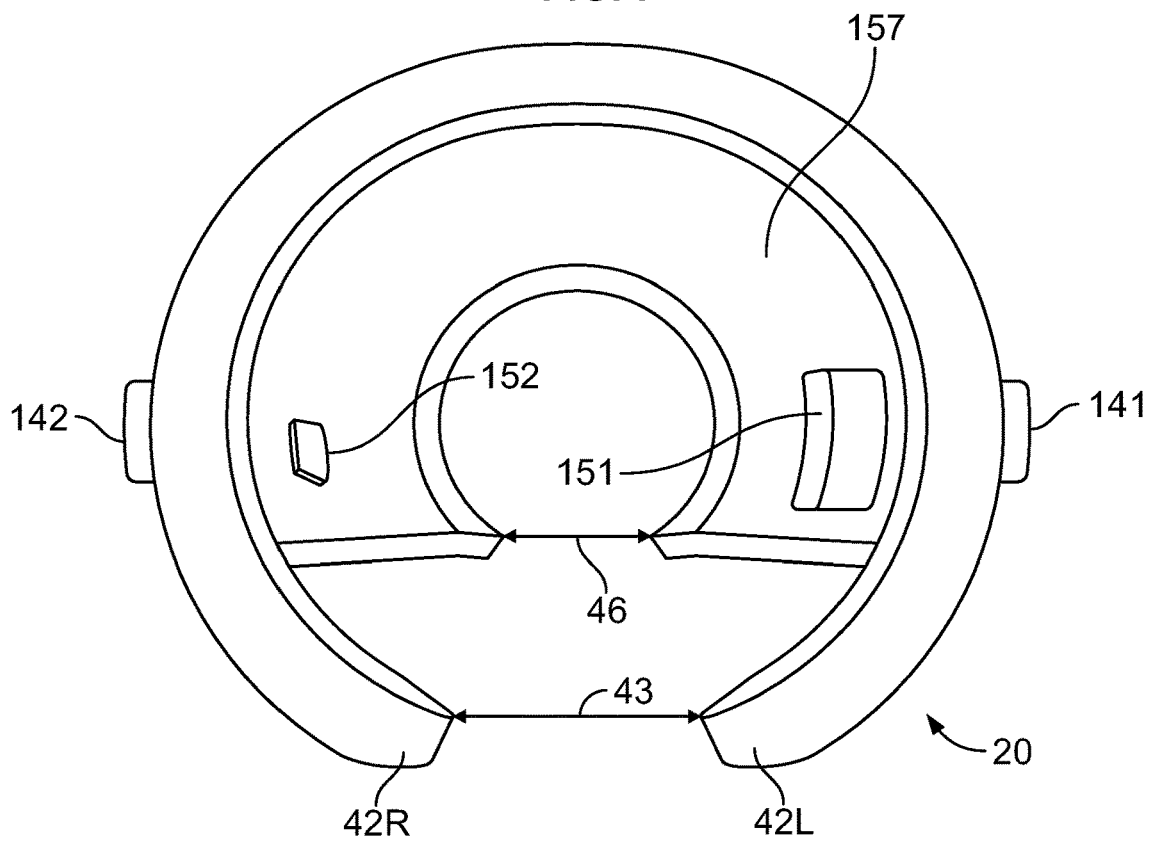
FIG. 8 is a bottom plan view of the sheath, looking in a tip-ward direction.

FIG. 8 is a bottom plan view of sheath 20, looking in a tip-ward direction. Internal stops 151 & 152 cooperate with surfaces and grooves on the syringe 5 to stop rotation of sheath 20 at various angles to syringe 5.

FIG. 9 is a front oblique view of sheath 20. This conveys the ramped and angled shape of stop 151. The angled surfaces of stop 151, include stop 151's front surface 151F, inside 153, and top 154. Sheath 20 has an inside wall 157.

Smaller stop 152 is seen through the translucent wall of sheath 20, as are thread segments 52, 53, and 56.

Figure 10:
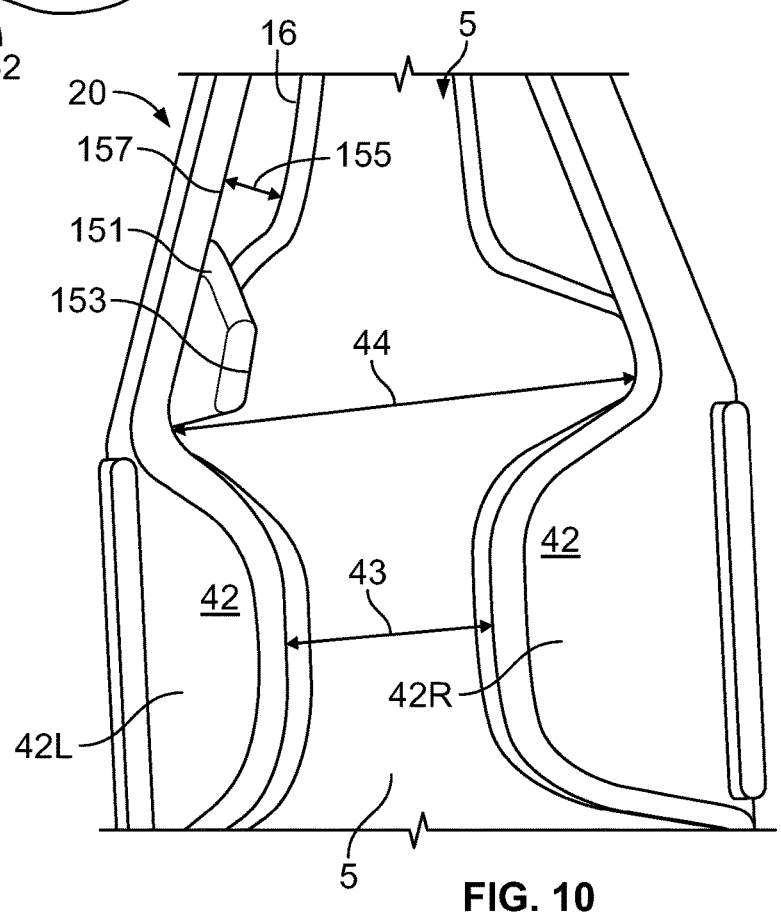
FIG. 10 shows clearance 155 between inside wall 157 of sheath 20, and outside of conical wall 16 of syringe 5.

FIG. 10 shows clearance 155 between inside wall 157 of sheath 20, and outside of conical wall 16 of syringe 5. In the position shown in FIG. 10, when the sheath 20 is being rotated onto syringe 5, and the lowest segment of the thread is engaged with the highest groove of the syringe 5, there is sufficient clearance 155 so that inside surface 153 of stop 151 almost clears the outside surface 16 of syringe 5, and provides only a gentle stop. Rotating sheath 20 tighter, expands flexible sheath 20, and allows sheath 20 to rotate another revolution, and ring-ward.

Because surface 157 approaches surface 16, the rotation becomes stiffer, until stop 151 (FIG. 11) drops into gap 200 (FIG. 12), at edge 201, at which point resistance drops.

Figure 12:
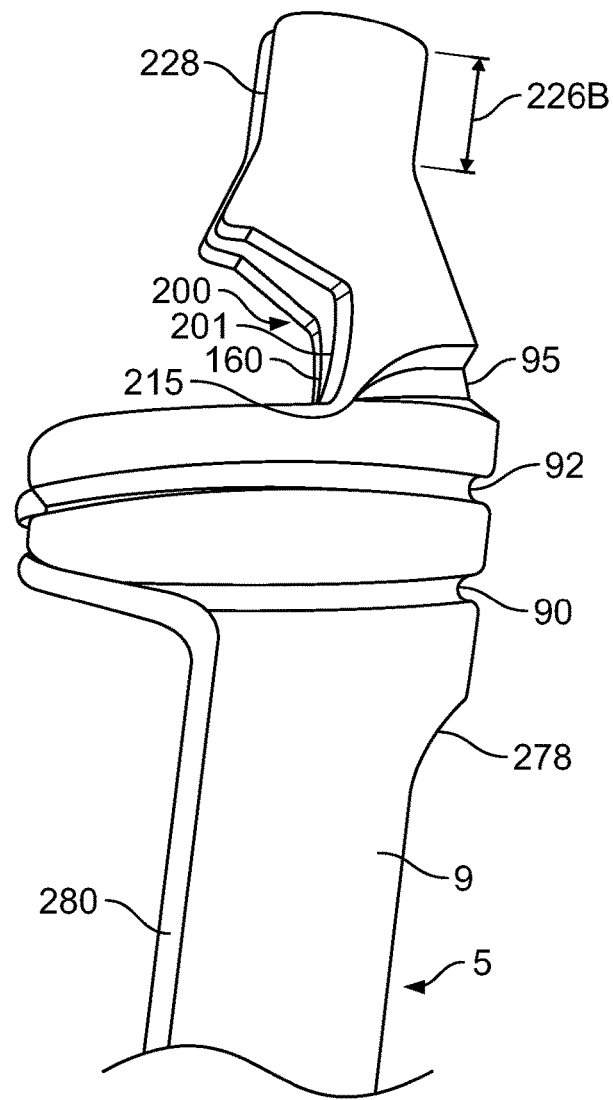
FIG. 12 is a side elevation of the syringe.
Figure 13:
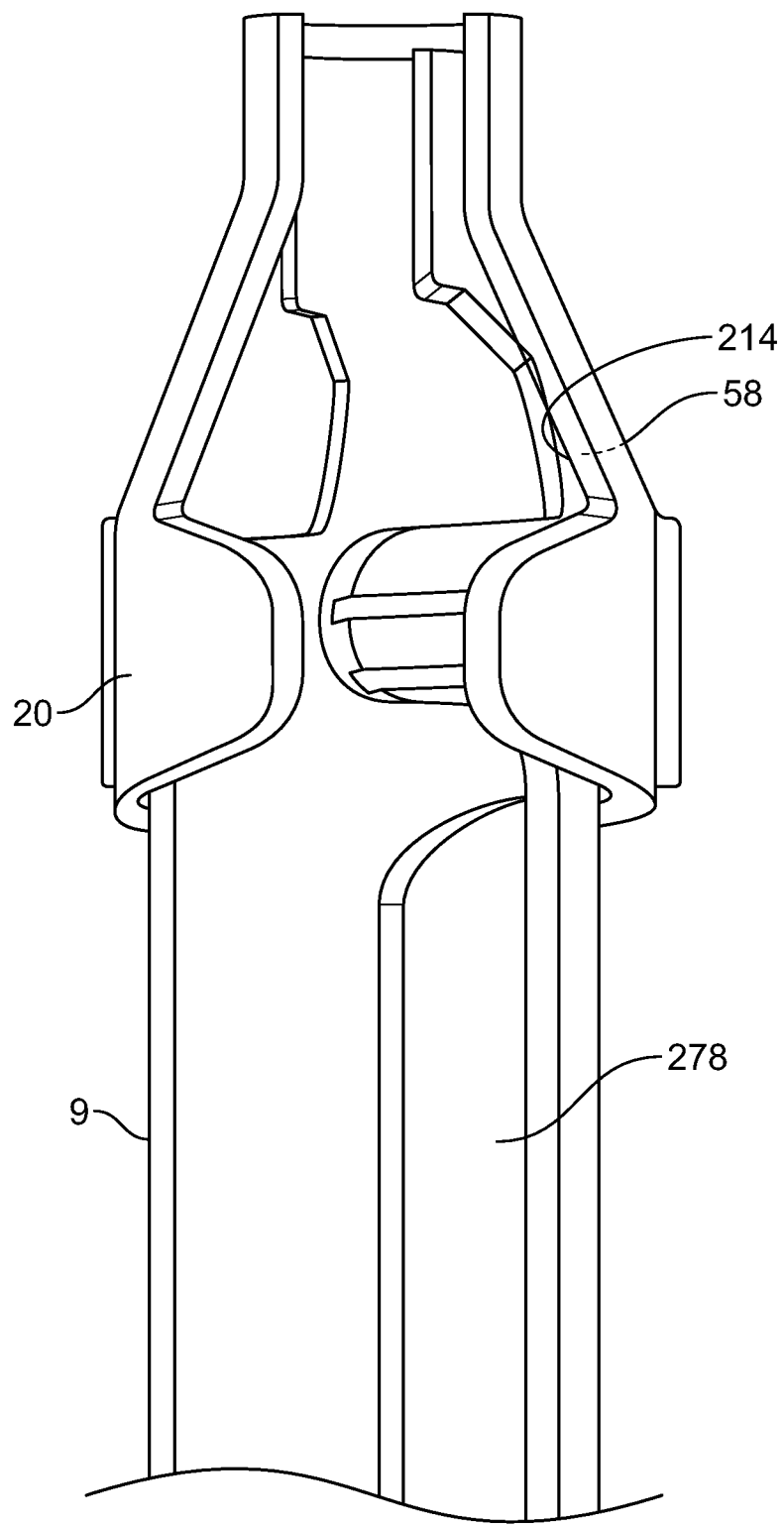
FIG. 13 is a front oblique side elevation of the sheath on the syringe.

At FIG. 13, topmost thread segment 58's leading point 214 (FIG. 13), is traveling along groove segment 95 (FIG. 12). But, leading point 214 encounters a constricted end 215 of groove 95, providing a low-resistance stop.

Increasing rotation force will force the sheath 20 to rotate again and accelerate briefly, as stop 152 (FIG. 8) drops into gap 200 (FIG. 12).

But, there is only about one millimeter of play before stop 151 stops hard against edge 160 (FIGS. 2 & 3). This centers sheath 20, so that sheath front wall gap 56 aligns with syringe front wall gap 64, (FIGS. 1 & 6) so that the needle assembly 14 can be inserted into the cone 16.

Figure 11:
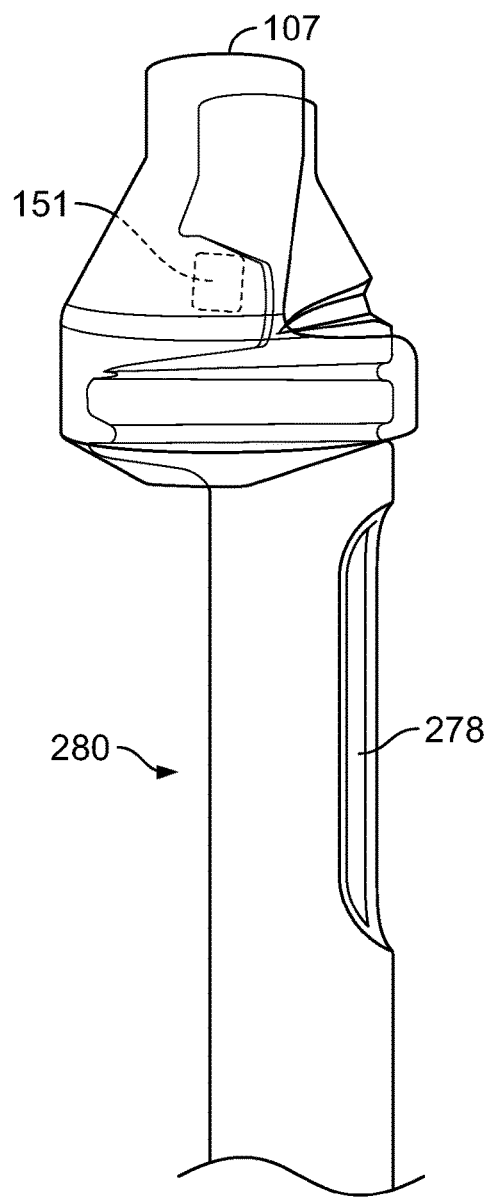
FIG. 11 is a side elevation of the sheath on the syringe.

After insertion of the cone 15, this sheath 20 will be rotated 180 degrees so that the incline of thread 50 and grooves 39 push the needle assembly 14 tip-ward, to the position shown in FIG. 11, thereby seating a conical segment 15 of the needle assembly 14, against a cooperatively shaped conical part 140 of the interior of the syringe's cone 16.

Figure 22:
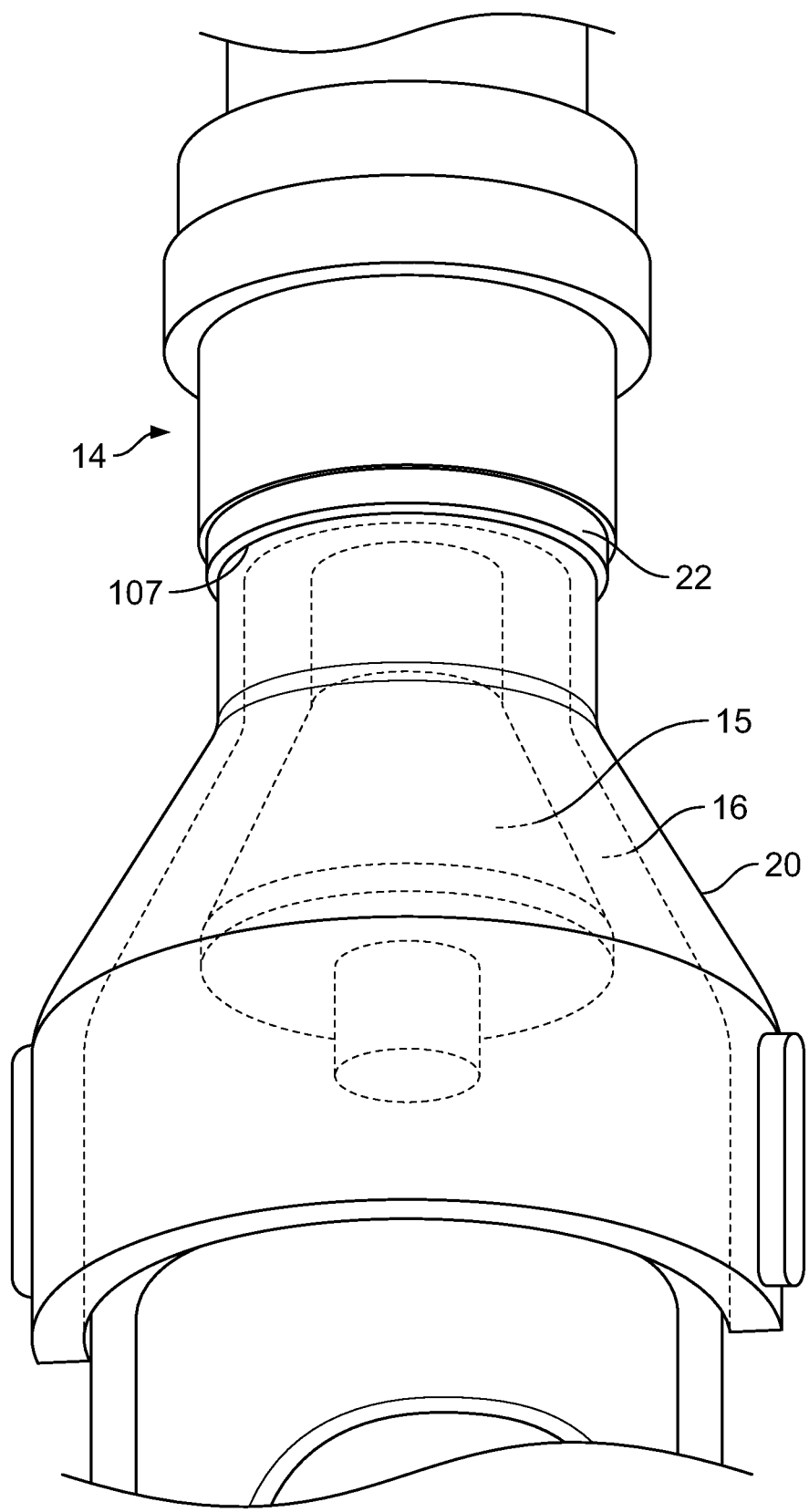
FIG. 22 is a perspective view of the syringe, with the sheath holding the needle assembly firmly in the syringe.

FIG. 22 shows how the top, or tip, or end 107 of sheath 20 abuts and pushes against flange 22 of needle assembly 14, thus seating needle's cone 15, firmly against the inside of syringe cone 16.

Sheath 20 will thus stabilize the needle assembly 14, and thereby facilitate installation of anesthetic medicine cartridges 12, and facilitate changing anesthetic medicine cartridges 12 during multiple injections.

Further tightening rotation of the sheath 20 will cause the flexible sheath's threads to jump the grooves on the syringe, allowing sheath 20 to move one groove ring-ward, and thereby relieve the seating pressure, and thereby allowing the needle assembly 14 to fall from the syringe 5 into a sharps container, not shown.

Alternatively, reversing rotation, to a loosening rotation of sheath 20, will relieve the seating pressure and allow the needle to fall from the syringe into a sharps container.

This sheath 20 can be made out of stainless steel sheet to meet the above criteria. The stainless steel sheet can remove the chrome plating after multiple uses; therefore, there must be no sharp edges to remove chrome plating.

FIG. 13 shows multiple grooves to stabilize of the sheath on the syringes to allow forward rotation (the activated position) and backward (the resting position). I have tried the grooves in the cone section of the syringes; however, the grooves in the cone section do not add to the stability. These grooves should not hinder the placement (or removal) of cartridges; therefore, the grooves should not be placed below the ribbon part of the syringe.

Figure 14:
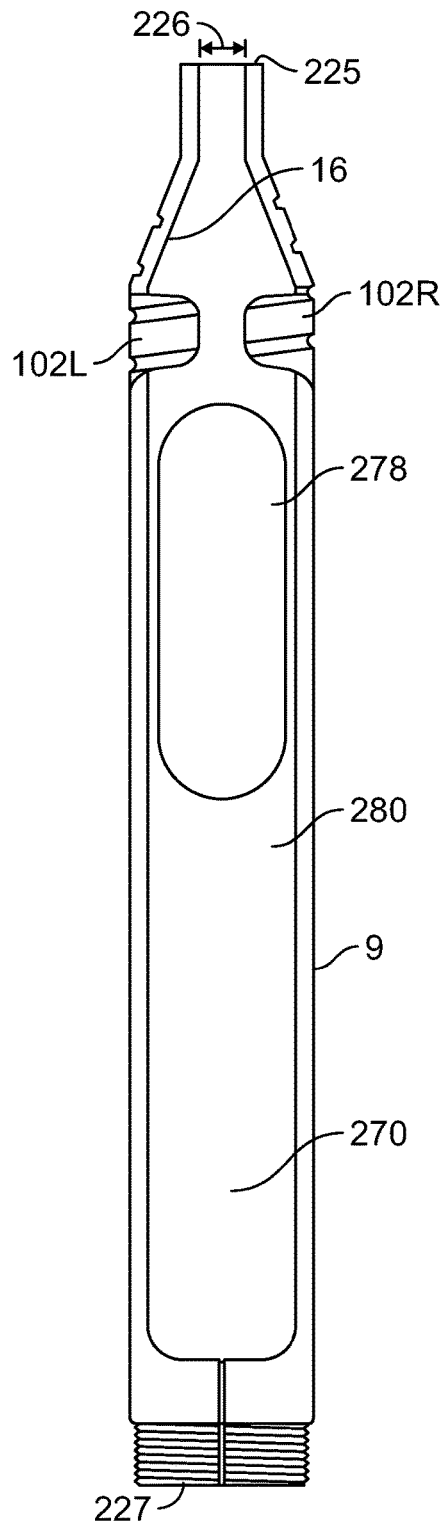
FIG. 14 is a front elevation of the syringe body.

FIG. 14 is a front elevation of an early embodiment of syringe body, generally designated 9, with threads running onto the cone.

Dimensions are provided in millimeters (mm). Body 9 has a tip-ward surface 225 measuring 5.2 mm across its outer diameter. Threads 227 at the bottom or ring-ward end of syringe body 9 can screw into finger grip 8 (FIG. 1), to assemble syringe body 9 to finger grip 8.

A 24.8 mm long slot 278 is provided, so that the user can change medicine cartridge 12 by:
  withdrawing the harpoon 11 FIG. 19, by pulling ring-ward the shaft 10, pulled ring-ward by actuator ring 7 (FIG. 1);
  holding the cartridge 12 through front opening 280 and ejection slot 278, preferably by placing the thumb of the same hand as the finger against the front of medicine cartridge 12, to grasp medicine cartridge 12;
  sliding medicine cartridge 12 ringward or away from cartridge needle 231, to disengage the cartridge 12 from cartridge needle 231; and
  out front opening 280, to free medicine cartridge 12 from cartridge needle 231;
  pushing through ejection slot 278 against the cartridge 12 to dislodge it, so that the cartridge 12 will drop into a waste container.

Figure 15:
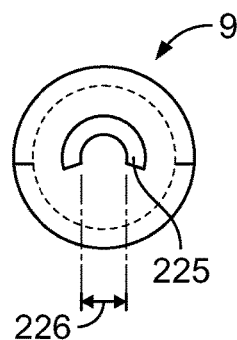
FIG. 15 is a top plan view thereof.

The original informal FIGS. 13-15, that were filed with the priority U.S. Provisional Patent Application 62/118,310, filed 19 Feb. 2015, and which have been incorporated by reference in all the subsequent applications, had dimensions marked on them in millimeters. We reserve the right to amend this specification to include those measurements.

FIG. 15 is a top plan view of syringe body 9, showing top surface 225 of syringe body 9.

Figure 16:
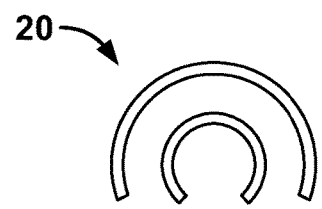
FIG. 16 is a top plan view of the sheath.

FIG. 16 is a top plan view of sheath 20.

Figure 17:
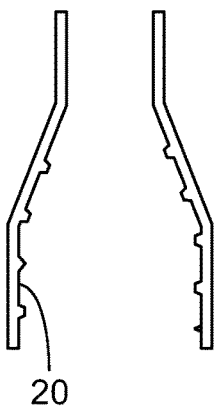
FIG. 17 is a front elevation thereof.

FIG. 17 is a front elevation of sheath 20.

Figure 18:
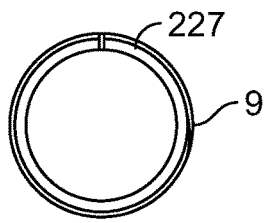
FIG. 18 is a plan view of the body.

FIG. 18 is a bottom plan view of syringe body 9, showing threads to mount the finger grip 8.

FIG. 19 is a front elevation of said syringe body 9 with plunger shaft 10 mounted on syringe body 9.

A collar 228 extends tip-ward from the syringe body 9. The collar 228 has a tip-ward edge 225.

A front collar opening 226 has a width 226A equal to the inner diameter of the collar 228. The front collar opening width 226 extends the axial length 226B of the collar 228.

FIG. 20 is a perspective view of a needle assembly 14. The needle assembly 14 is assembled.

Figure 21:
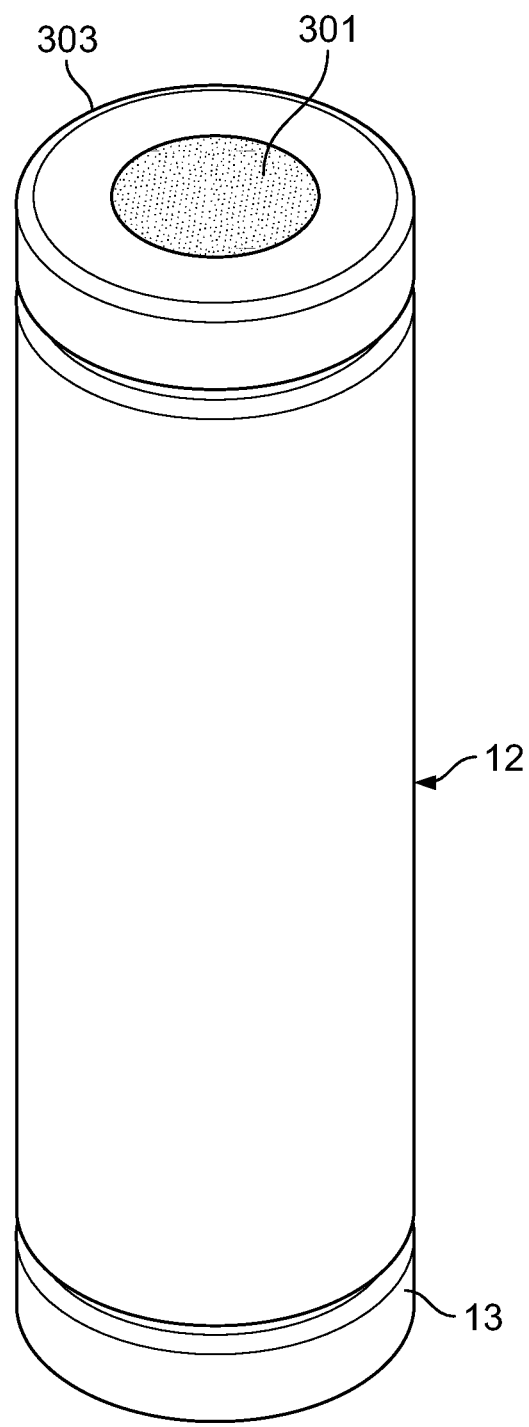
FIG. 21 is a perspective view of the medicine cartridge.

FIG. 21A shows needle assembly 14 is in three pieces on the right. Needle 31 is part of a needle tube 14A.

The opposite end of needle tube 14A is a second needle or cartridge needle 231 in fluid communication through needle tube 14A with needle 31, at the ring-ward end of needle assembly 14, under protective cap 238, when assembled.

Cartridge needle 231 is exposed, when uncapped, so that it may impale a diaphragm 301, atop cap 303 at a tip-ward end of medicine cartridge 12, establishing fluid communication from the medicine cartridge to the hollow needle tube 14A.

Needle tube molded body 14B reinforces needle 31. Self-aspirating cylinder 240 reinforces the needle tube 14A at its cartridge-ward end. Self-aspirating cylinder 240 creates a self-aspirating effect when pressure on the actuator ring is relaxed, by allowing the cartridge diaphragm to relax and expand the cartridge interior volume to reduce atmospheric pressure within the cartridge, and suck back some blood, into the cartridge, if the needle 31 tip 34 is in a blood vessel.

Cone 15 is tip-ward of self-aspirating cylinder 240.

A second cylinder 244 is tip-ward of cone 15. This cylindrical form, second cylinder 244 carries tip-ward to the flange 22. Flange 22 is provided, for sheath 20's pushing against, as in FIG. 22. In FIG. 20, a plurality of six fins 251 reinforces domed cylinder 248 and flange 22. Fins 251 provide a snug fit to protective ring-ward cap 38.

Domed cylinder 248 reinforces needle 31 tip-ward to domed cylinder 248's tip-ward end, past which, needle 31 is bare.

When ring-ward cap 238 is in its protective position:
  widest part 252 of cone 15 fits snugly against cap 238 in place; and
  238's rim 260 abuts against a flange 22.

From tip-ward, in a plan view, the six fins 251 resemble an asterisk.

To install the needle assembly 14 onto the syringe, sheath 20 is snapped onto syringe body 9, as in FIG. 6, and syringe front walls 102L and 102R are aligned with sheath front walls 42L & 42R, to allow needle assembly 14 to pass through the gap formed between the left and right front walls of the sheath and the syringe.

Ring-ward protective cap 238 is removed from lower or ring-ward needle 231 to expose ring-ward cartridge needle 231. The needle assembly 14 is placed with its cone 15 through the aligned front openings of syringe and sheath, with conical portion 15 of the needle assembly 14. Conical portion 15 is then seated inside the matching conical end 16 of syringe body 9, as in FIGS. 1 and 6.

Sheath 20 is then rotated in a clockwise direction, when viewed from the actuator ring 7, to be positioned as in FIG. 22, causing end 107 of sheath 20 screw to tip-ward, against flange 22, forcing the needle assembly 14, still-capped by needle-cap 38, tip-ward, so that cone 15 seats firmly against the inside of syringe cone 16, holding the needle assembly 14 firmly in place in the syringe body 9. The front gap of the sheath 20 is now aligned diametrically opposite to the front gap of syringe body 9, which closes the front opening 280. In the presently preferred embodiment, this is a 180 degree rotation from the open position.

Thumb ring 7 (FIG. 1) is then pulled ring-ward to clear the harpoon 11 (FIGS. 1 & 19), from the compartment 270 for the medicine cartridge 12, thus providing room for the medicine cartridge 12 to be inserted through opening 280 (FIG. 19).

Through the front opening 280 of compartment 270 (FIGS. 14 & 19), medicine cartridge 12 is then installed, and positioned as shown in FIG. 1.

Thumb ring 7 is then pressed by the user, tip-ward towards the needle;

driving shaft 10 and harpoon 11 into slidable seal 13 (FIG. 21) of medicine cartridge 12;

driving the medicine cartridge 12 toward the needle assembly 14; and impaling the tip-ward diaphragm 301, located in cap 330 of the medicine cartridge 12, by impaling the tip-ward diaphragm 301 on cartridge needle 231 of FIG. 20; and creating fluid communication between the medicine in medicine cartridge 12 and the hollow needle 31 and its hollow point 311 at tip 34.

Medicine cartridge 12 may thereafter be changed for this patient. Thumb ring 7 is withdrawn as far as possible which pulls harpoon 11 out of slidable seal 13 and provides clearance of the cartridge, probably disengaging the cartridge from cartridge needle 231.

If the cartridge 12 as not come loose of harpoon 11, the cartridge is grasped between a thumb (through opening 280) and forefinger (through opening 278), and pulled tip-ward from harpoon 11.

Syringe 5 can then be turned front side down. Medicine cartridge 21 will then fall through opening 280 out of compartment 270.

A new medicine cartridge 12 may then be inserted as described above.

When the patient is done being anesthetized, the last cartridge can be removed, sheath 20 can be rotated in either direction, which will either:

twist sheath 20 away from flange 22 on needle assembly 14; or allow with threads to jump next lower groove segment.

Either way, the pressure holding the flange 22 tip-ward, and holding cone 15 in its seat 16, is relieved. Then the syringe can be turned, front-down, allowing the needle assembly 14 to drop out of the syringe 5 into a sharps container.

The Slope of the Grooves.

The limitation of the activation position will be when the sheath 20 pushes the needle assembly 14 against the end of the syringe 5. But the slope of the grooves has to be such that, for a 120-degree rotation, the forward, or tip-ward, traveling length (from the resting to the activated position) is about 1.8-2.0 mm.

Sharps De-Tipping System

New matter in the United States Bypass Continuation-in part application follows. The new matter comprises a system of removing the needle 31 from the syringe 3.

Figure 23:
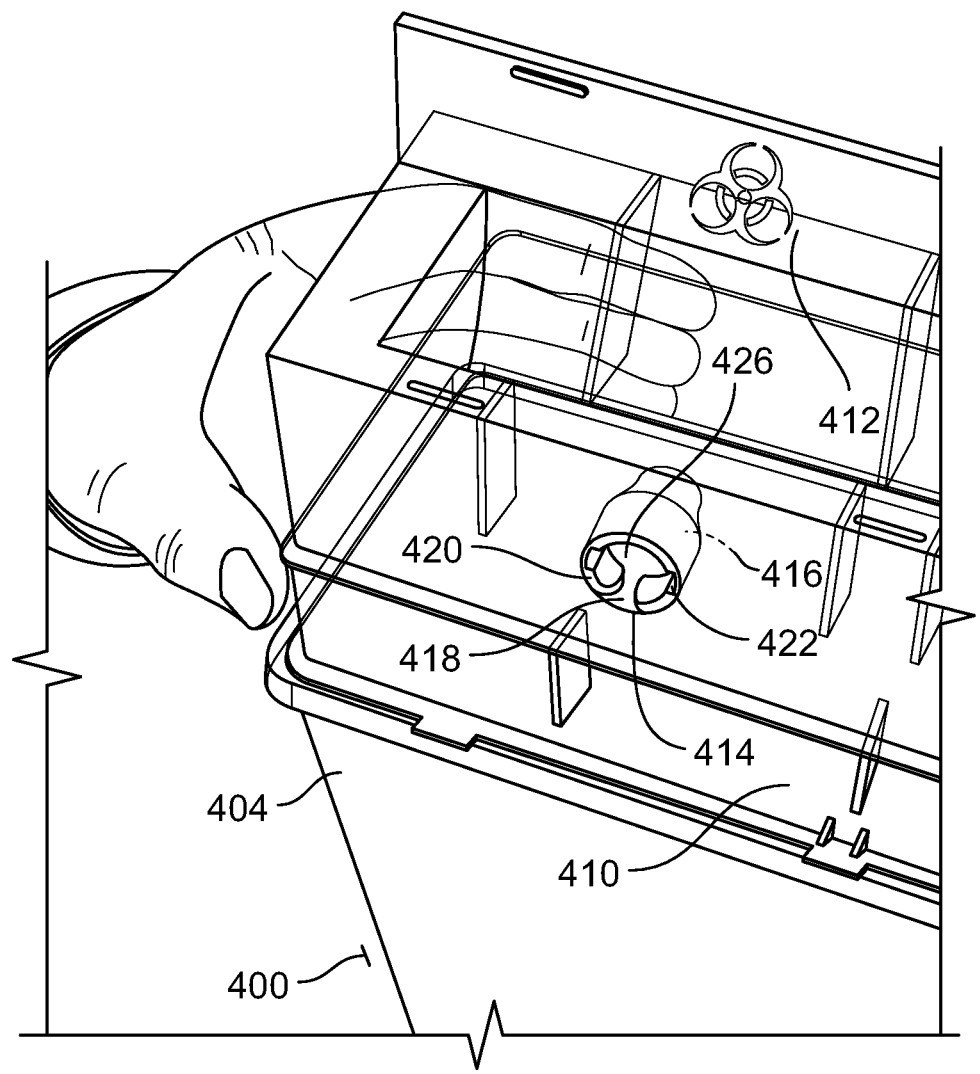
FIG. 23 is a perspective view of a sharps container.

FIG. 23 shows a sharps container generally designated 400. The sharps container comprises a sharps container bottom 404.

Atop to the sharps container bottom portion 404 is removably attached a sharps container in top 410. This conventionally includes a sharp container lid 412.

Sharps socket 414 is a novel part of this sharps container 400.

Sharps socket 414 has a front opening 418.

A left notch 420 and a right notch 422 in the opening 418 of socket 414 are configured to engage exterior ribs 141 & 142, said ribs for facilitating finger grip on the outside of sheath 20, shown in FIGS. 7 and 8.

Figure 24:
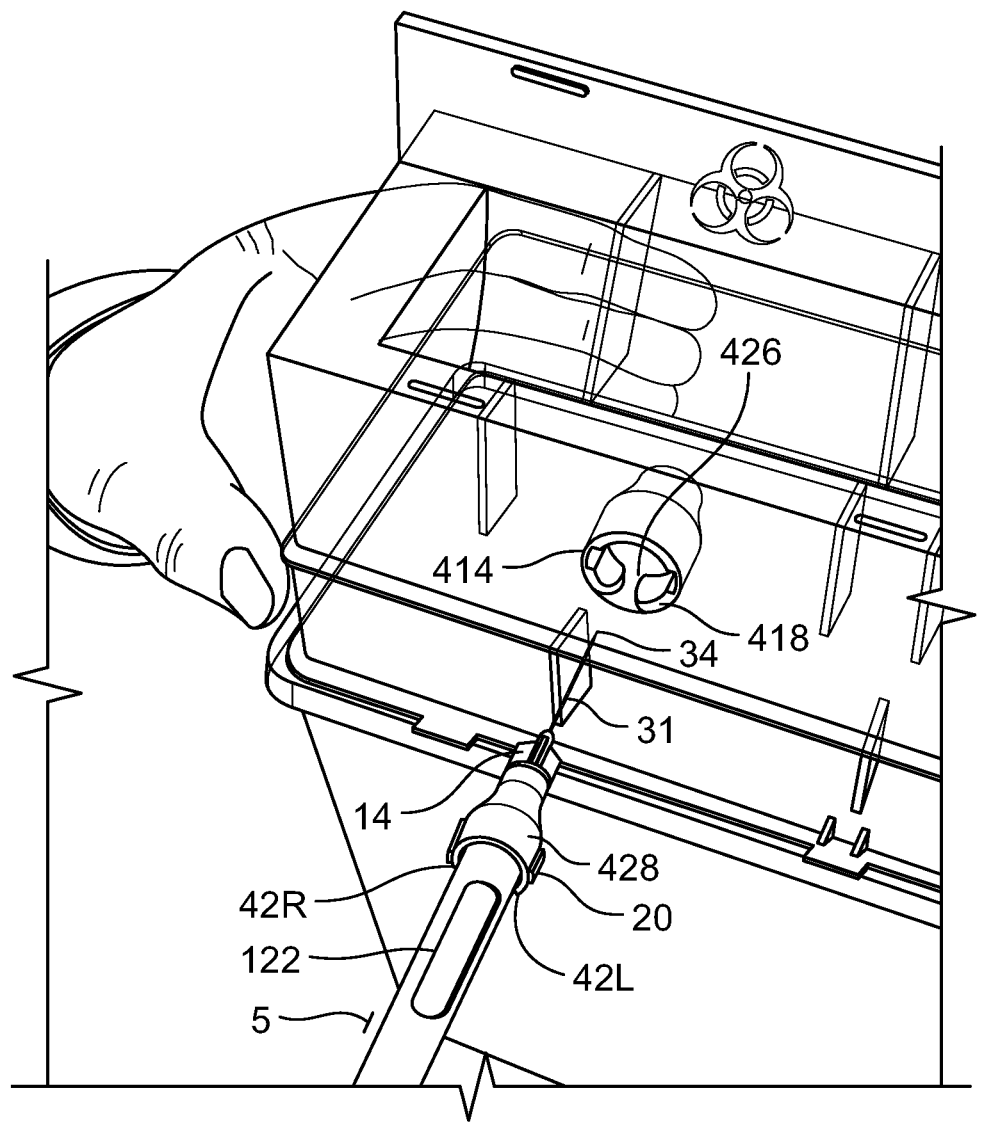
FIGS. 24-30 are perspective views of a sharps container and syringe while de-tipping.

As shown in FIG. 24, socket 414 has an interior surface 426 is configured to closely receive and frictionally engage an outer surface 428 of sheath 20.

FIG. 24 shows the syringe, generally designated 5, without its medicine cartridge, shown in FIG. 1 as medicine cartridge 12.

FIG. 24 shows the needle assembly 14 held in place by sheath 20. Screw threads that have been detailed in FIGS. 2 through 5, are holding the flange 22 by sheath 20's pushing against the flange 22, as in FIG. 22.

In FIG. 24, a user directs tip 34 of the needle 31 towards the socket front opening 418. Once the tip 34 is inside the opening 418, then needle 31, needle assembly 14, and sheath 20 help guide sheath 20 into the socket 414.

The front 42 of sheath 20 is closed at gaps at 43, 44 (FIG. 10), and 45 to 46 (FIG. 9), to prevent needle assembly 14 from escaping the front body opening 122 in the syringe body 9.

Figure 25:
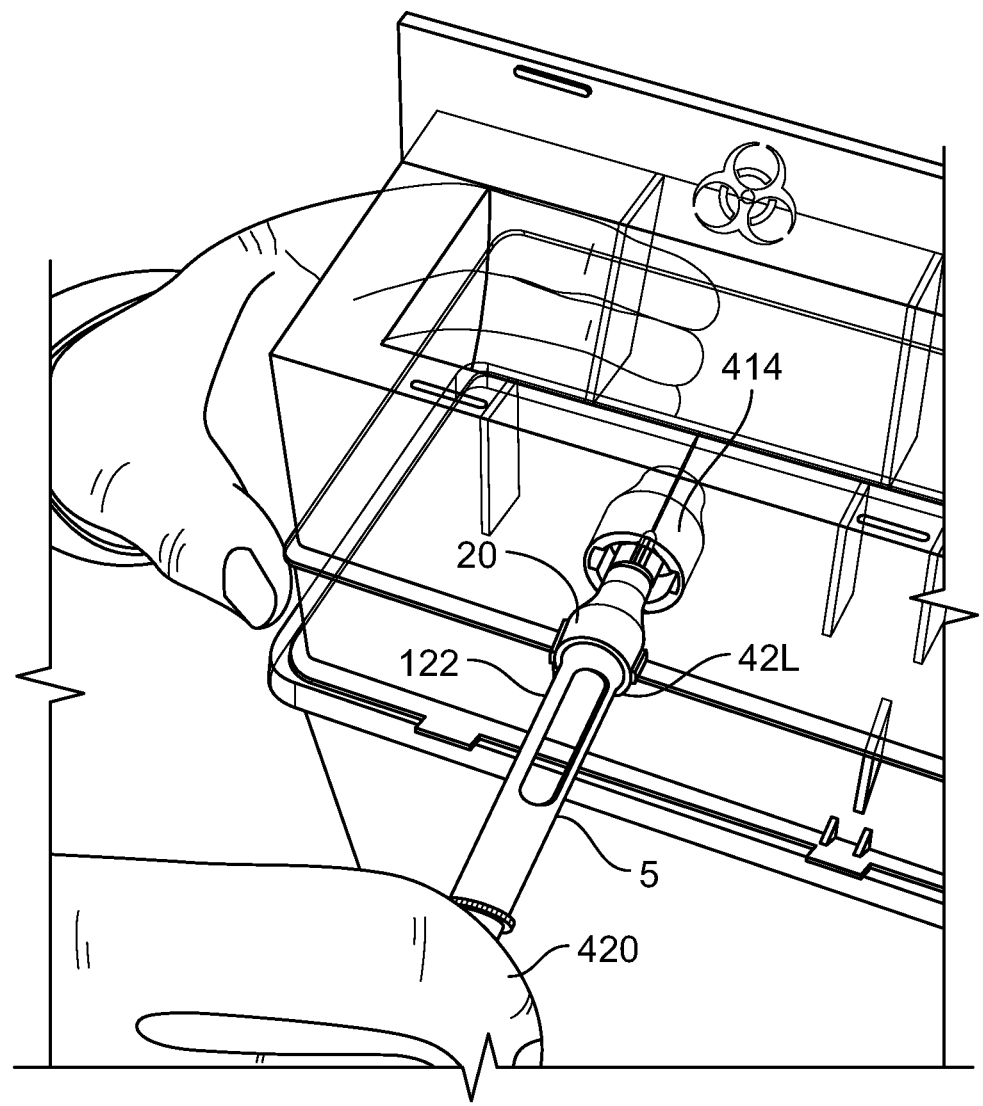

FIG. 25 shows a user 430 inserting sheath 20 into socket 414.

Figure 26:
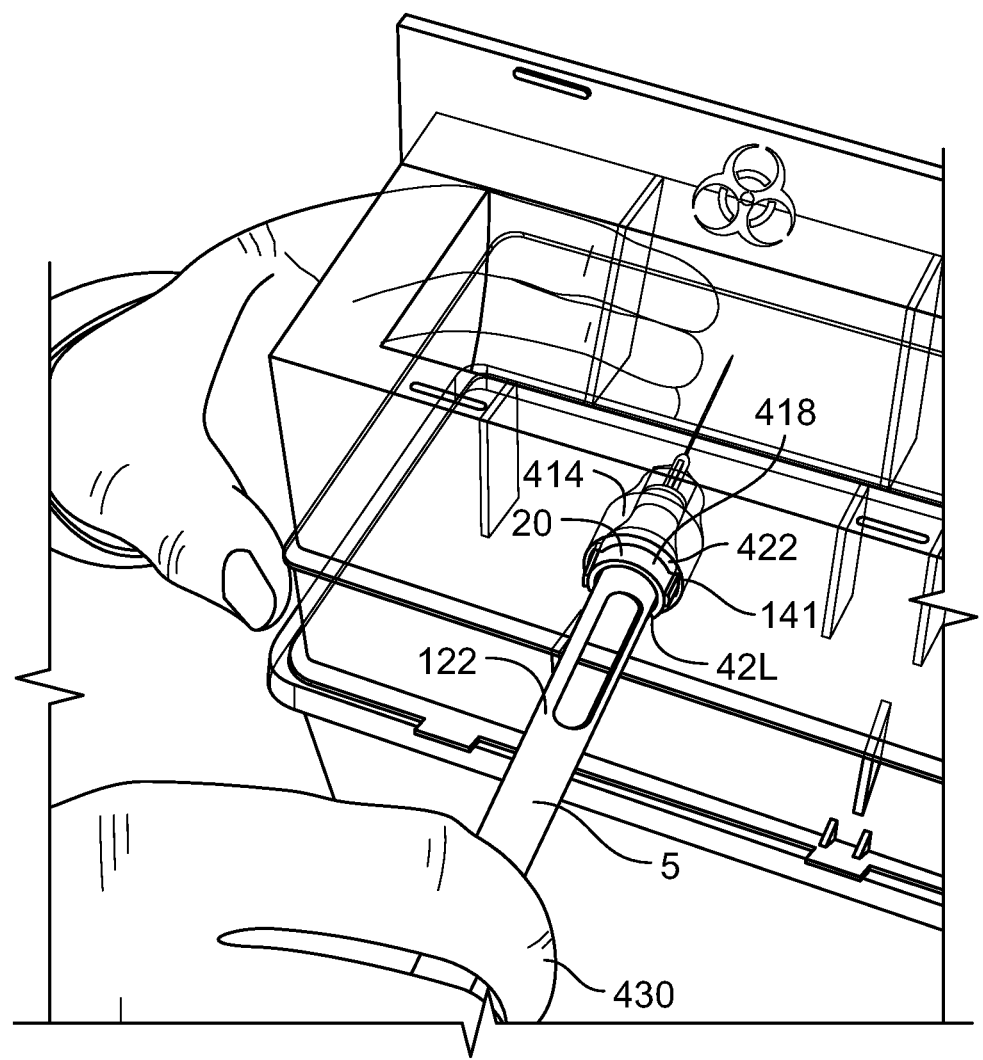

FIG. 26 shows rib 42L entering notch 141 in sharps socket 414, pushed by the user 430. Socket 20, at this angle shows an edge 42L of socket 20's sidewall defining a gap which does not align with front body opening 122. The rib 141 is fully inserted into notch 422 which prevents the sheath 20 from rotating with syringe 5.

Figure 27:
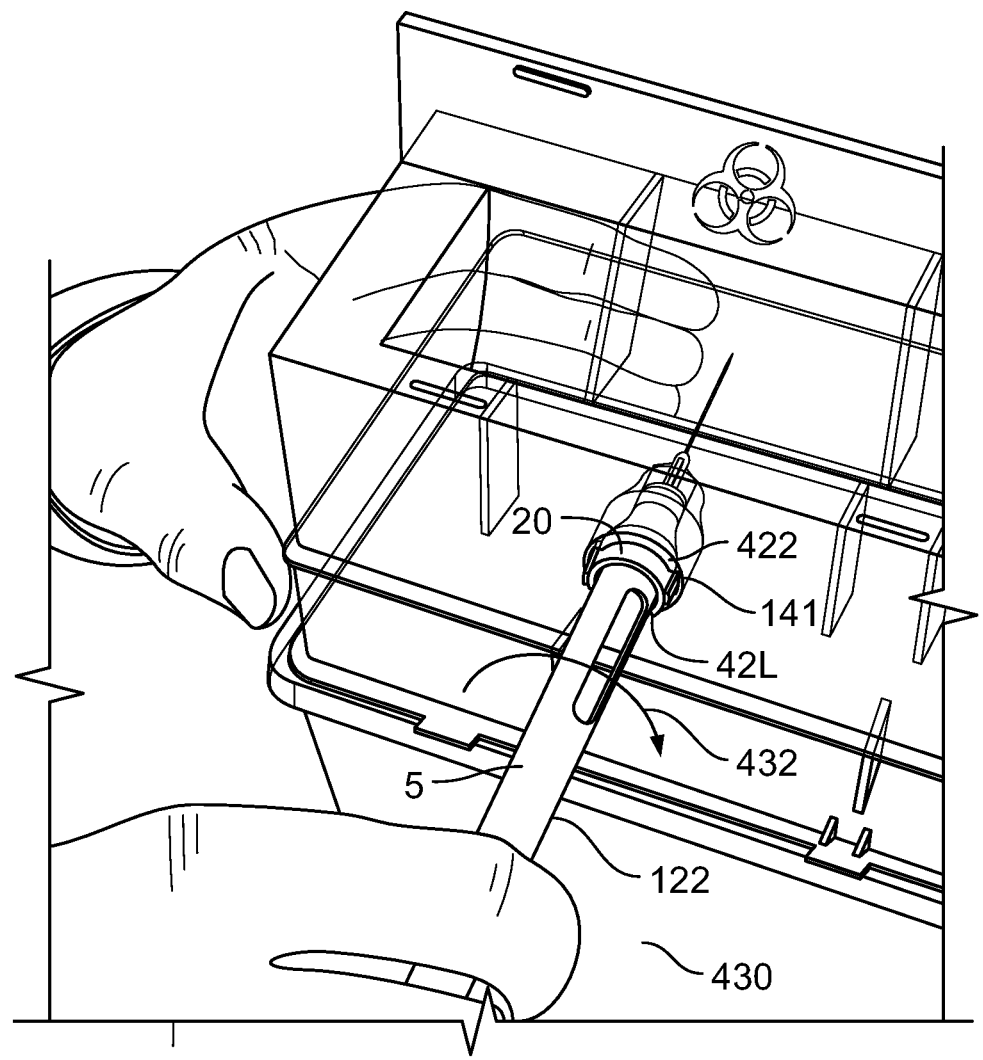

In FIG. 27, user 430 has begun rotating syringe 5 in a clockwise direction 432. This rotation eventually causes the internal threads 52-58 of the sheath 21 to jump the grooves 91-95 of the syringe body 9 (see FIG. 5) and to relieve pressure on flange 22 of the needle assembly 14 shown in FIG. 20A.

Had syringe body 5 been rotated counterclockwise, the counterclockwise rotation would unscrew the internal threads 52-58 of the sheath 20 from the grooves 91-95 of the syringe body 9 (see FIG. 5) and in that way to also relieve pressure on flange 22 of the needle assembly 14 shown in FIG. 20A.

Figure 28:
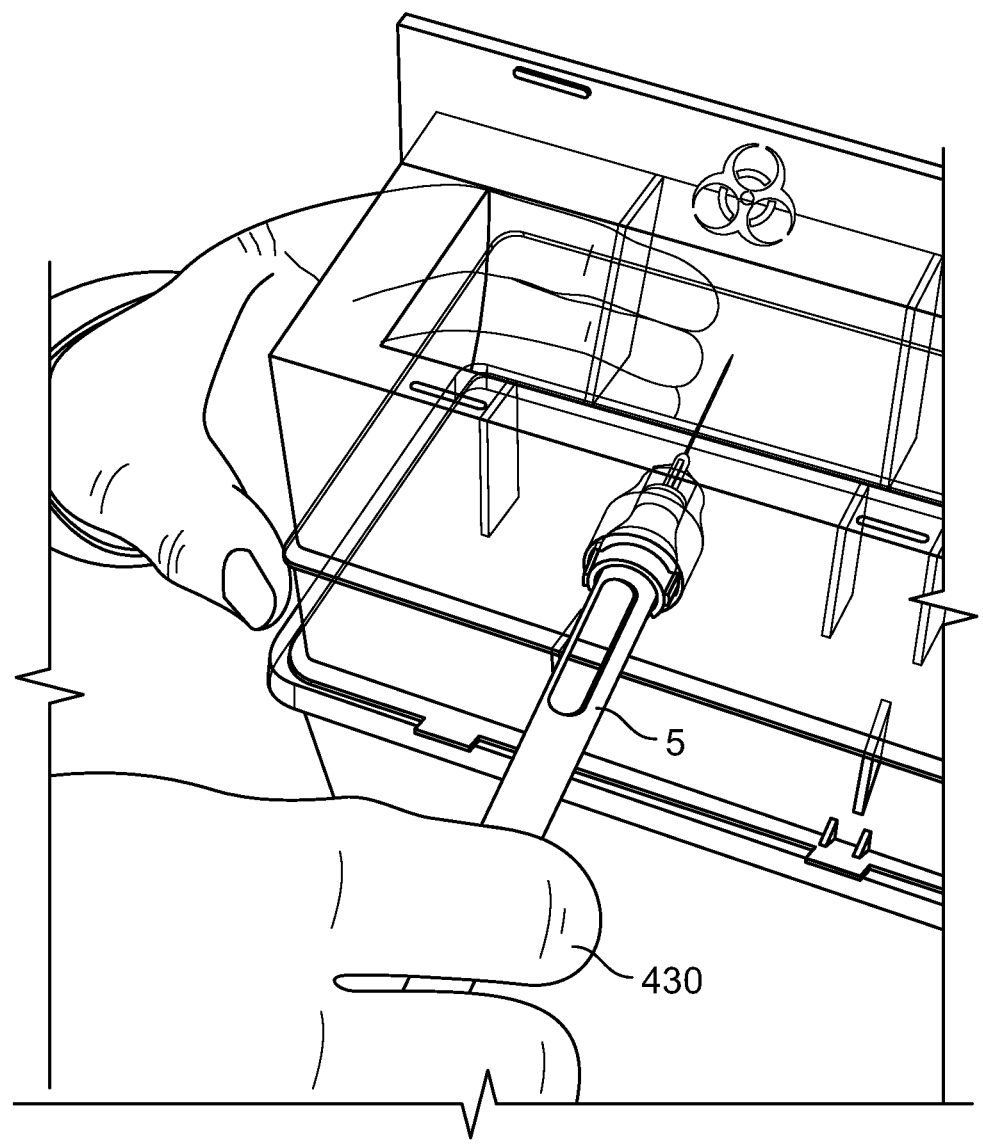

In FIG. 28, syringe 5 has been rotated 180° from its original position. Opening 122 is now beneath the syringe 5 and is aligned with the opening in sheath 20. Pressure has been relieved from the flange 22; and a lack of tension against seat 15 allowed needle assembly 14 to fall through the gaps of syringe 5, and through sheath 20, through socket 414, into the bottom 404 of the sharps container 400 shown in FIG. 29.

Figure 29:
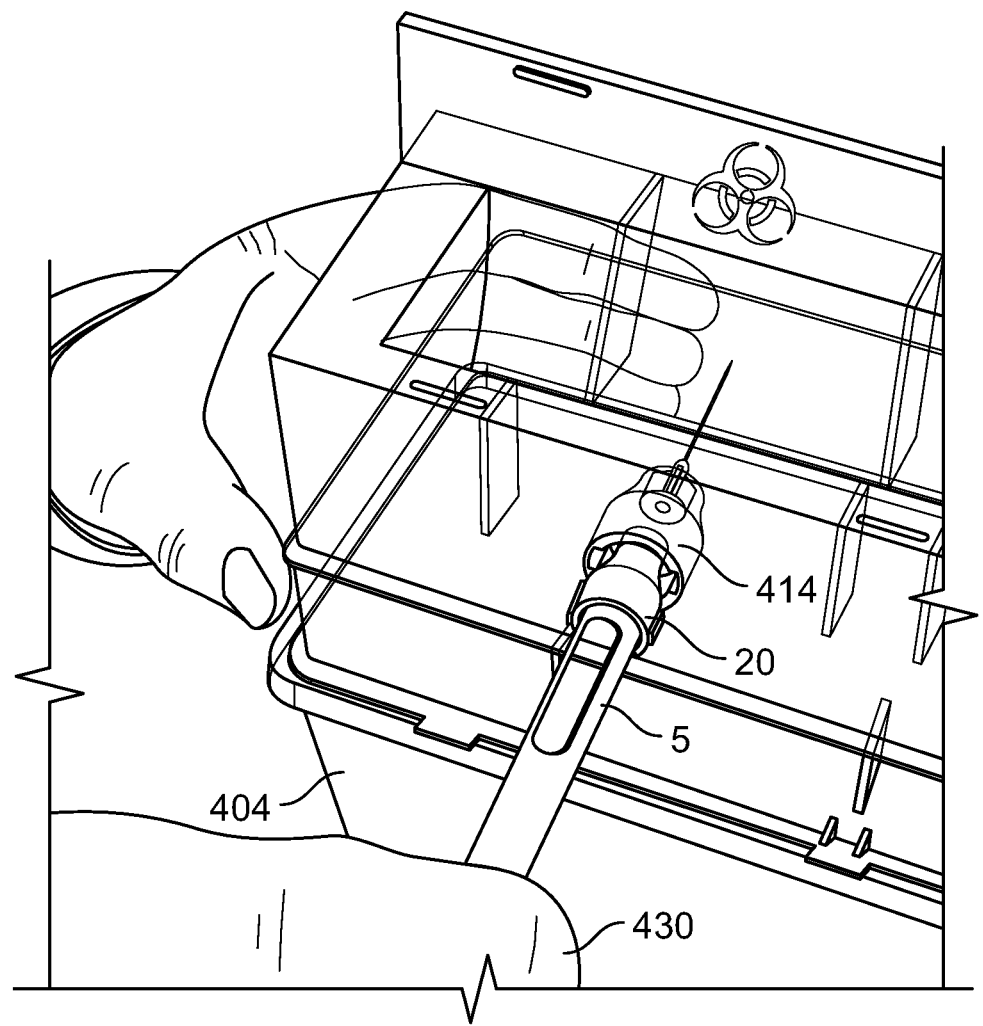

Therefore, in FIG. 29, no needle assembly is visible as syringe 5 is withdrawn from the sharps socket 414. In FIG. 29 user 430 has partially withdrawn syringe 5 and its sheath 20 from the sharps socket 414.

Figure 30:
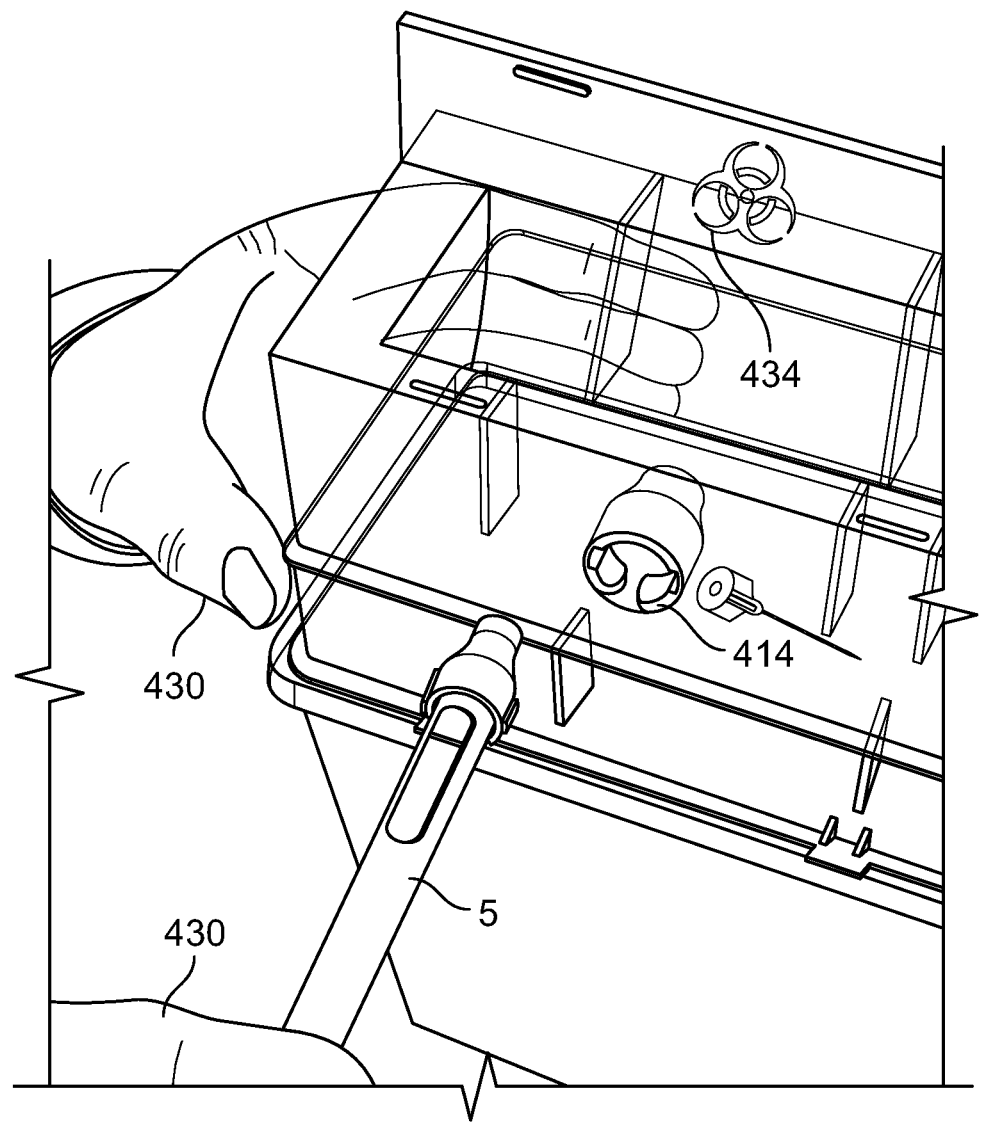

FIG. 30 is a somewhat blurred photo, as user 430 is rapidly withdrawing syringe 5 from socket 414. Again, no needle assembly. nor needle Is visible as syringe 5 is withdrawn from the sharps socket 414. This figure also shows the biohazard symbol for 434 on the lid of the sharps container.

Figure 31:
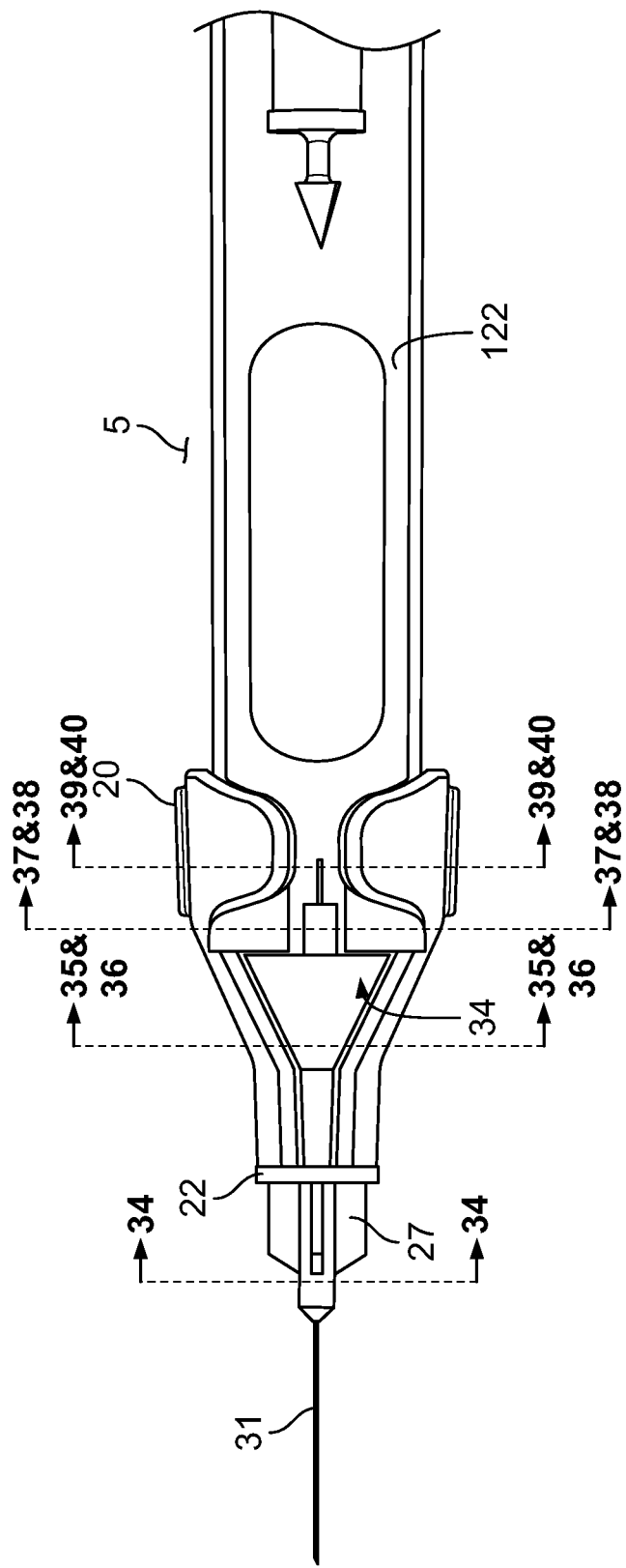
FIGS. 31-33 are side elevations of the syringe.
Figure 34:
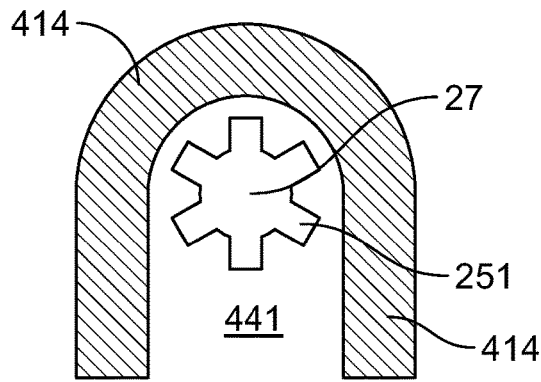
FIGS. 34-40 are cross sections taken through planes defined in FIGS. 31 and 33

FIG. 31 shows the syringe with the sheath and needle assembly, and shows four planes that are shown in cross section in FIGS. 33 through 40:

Plane A shown in FIG. 34.
Plane B shown in FIGS. 35 and 36.
Plane D shown in FIGS. 37 and 38.
Plane C. shown in FIGS. 39 and 40.

Figure 32:
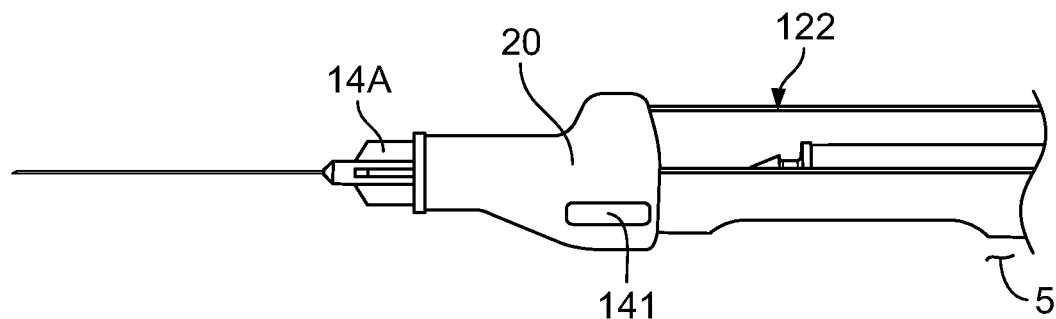

FIG. 32 is a side elevation of needle assembly with sheath 20 showing rib 141 and body front opening 122. The syringe 5 should be inserted in the sharps container 400 body with its body front opening 122 up. If the sheath 20's opening 43 is down, securing the needle assembly 14 to the syringe 5, then the sheath opening will be facing down, towards the sharps container bottom 404.

Figure 33:
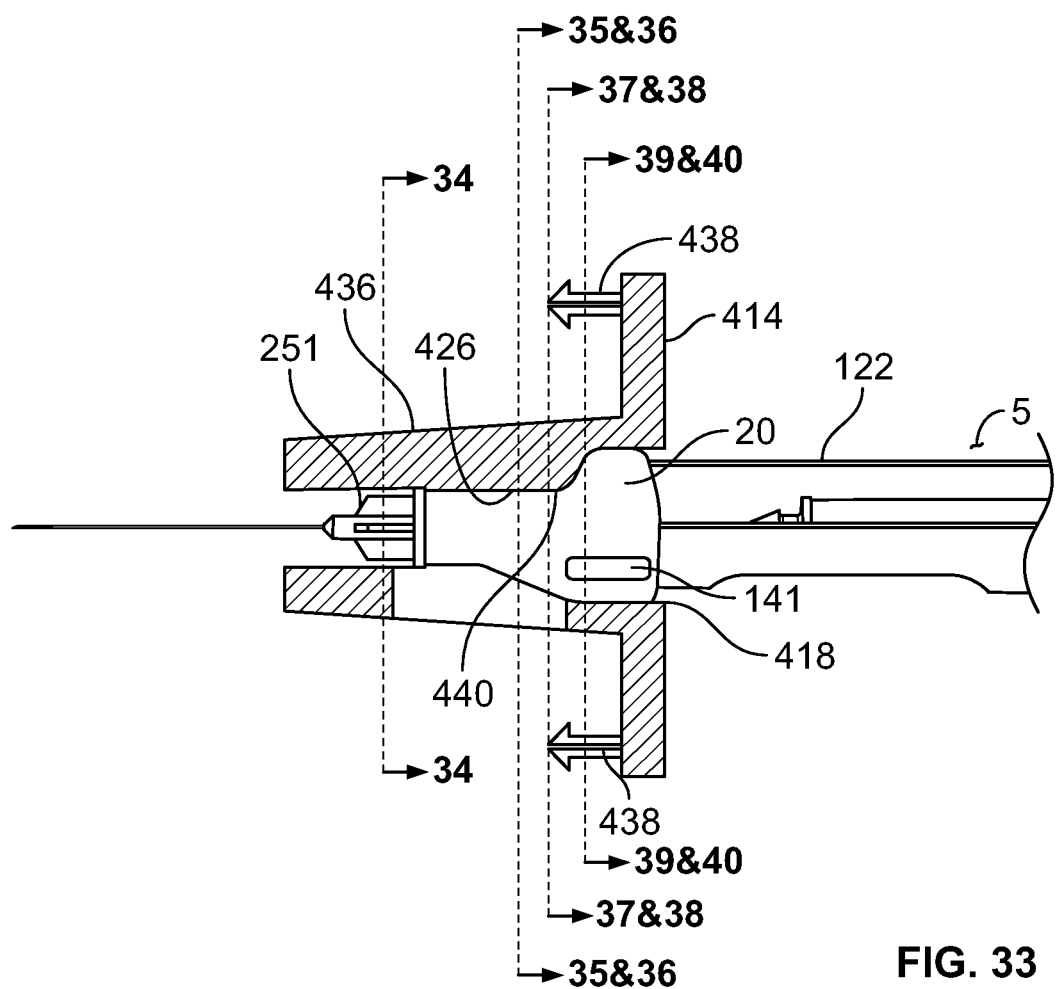

FIG. 33 is a cross-section of socket 414, but a side elevation of the outside surface 440 of sheath 20, fitted within socket 414. The close cooperative relation and snug fit, between:
sheath 440's inner surface 426, and
the sheath 20's external surface 440,
is clearly seen in FIG. 33.

Figure 35:
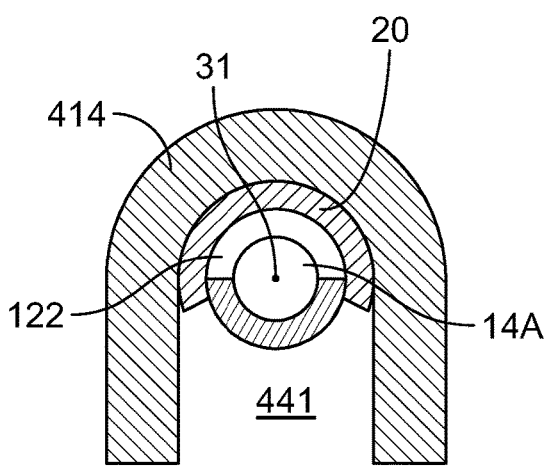
Figure 36:
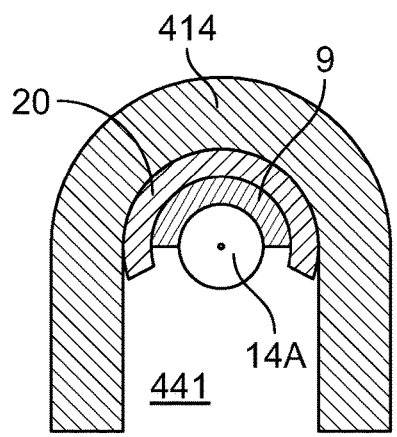
Figure 37:
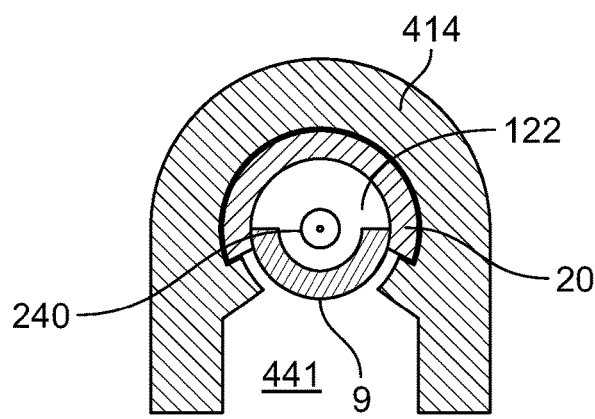
Figure 38:
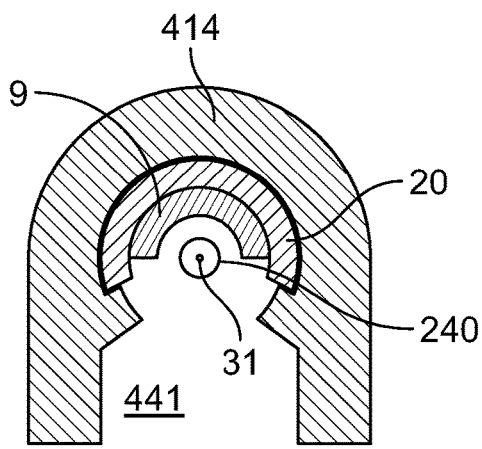

FIG. 33 again defines cross sectional planes:
plane A of FIG. 34,
plane B of FIGS. 35 and 36, and
plane C of FIGS. 37 and 38; this time with the sheath 20 inserted into socket 414.

Socket 414 is preferably made of polypropylene, as is the sharps container 400. Snap-in fasteners 438 may protrude from the container-side of the socket 414. The snap-in fasteners 438 will snap into cooperatively sized fastener holes 439 in the sharps container top 410.

Socket 414 comprises a socket bottom opening 441 (FIG. 42) in its bottom, for the sharps, also called the needle assembly 14, to fall through, towards the sharps container bottom 404.

FIG. 34 is a cross section through plane A. of FIG. 33. Reinforcing fins 251 are visible in this cross-section.

FIG. 35 is a cross-section of socket 414 at plane B of FIG. 33, showing the needle 31 passing through the needle assembly 14 at conical section 15. Sheath 20 closes body front opening 122 of metal frame 9, so that the needle assembly 14 cannot fall out in this position.

FIG. 36 is similar to FIG. 35. FIG. 36 shows the syringe 9, rotated 180° from FIG. 35, and thus oriented so that sheath 20's opening 43 coincides with the syringe 5's body front opening 122 of frame 9; and therefore, needle assembly 14 is free to drop out of the socket 414's socket bottom opening 441 and into the bottom 404 of the sharps container 400.

FIG. 37 is a cross-section of socket 414 at plane D of FIG. 33; displaying the ring-ward self-aspirating cylinder 240 on the needle assembly 14. The Self-aspirating cylinder 240 assists in self-aspiration of the needle. Self-aspiration enables the needle to withdraw any blood which may be in a blood vessel, if needle tip 34 is in a blood vessel. Such withdrawn blood can be seen in the medicine cartridge, through the body front opening or the back window. If blood is visible in the medicine cartridge, then the needle 31 must be withdrawn from the injection site, and inserted in an area where the needle 31 cannot inject anesthetic into a blood vessel. Injection of anesthetic into a blood vessel can cause unconsciousness, systemic reaction, or death.

In FIG. 37 the front body opening 122 of metal frame 9 does not coincide with open gaps of sheath 20, so that the needle assembly 14 cannot fall out.

FIG. 38 is similar to FIG. 37, a cross-section of socket 414 at plane D of FIG. 33. FIG. 38 shows the syringe 9, rotated 180° from FIG. 37, and thus oriented so that sheath 20's opening 43 coincides with the syringe 5's body front opening 122 of frame 9; and thus, needle assembly 14 is free to drop out of the socket 414, through socket bottom opening 441, and into the bottom 404 of the sharps container 400.

Figure 39:
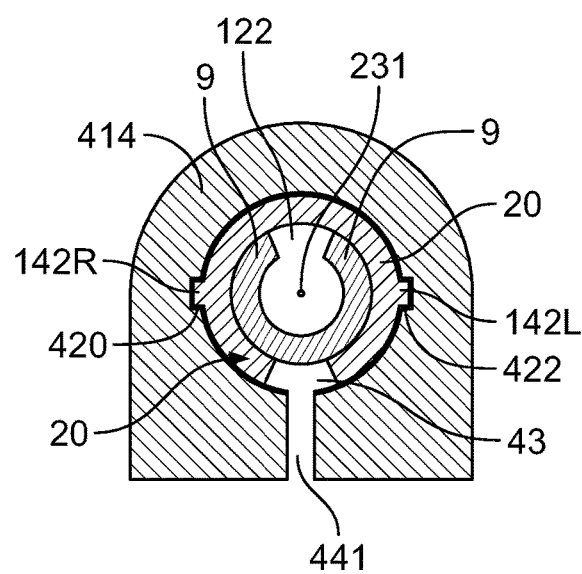

FIG. 39 is a cross-section of socket 414 at plane C of FIG. 33. In FIG. 39 the front body opening 122 of metal frame 9 does not coincide with open gaps of sheath 20, so that the needle assembly 14 cannot fall out. Sheath 20 comprises sheath ribs 142R and 142L. At this plane C, socket 414 comprises cooperating grooves 420 & 422, into which ribs 142R and 142L fit snugly, to prevent rotation of sheath 20, relative to socket 414. Thus, when syringe 5 and metal frame 9 are rotated 180°, as shown in FIG. 40, sheath 20 maintains its rotational position in the socket 414, with socket bottom opening 441 aligned with sheath opening.

Figure 40:
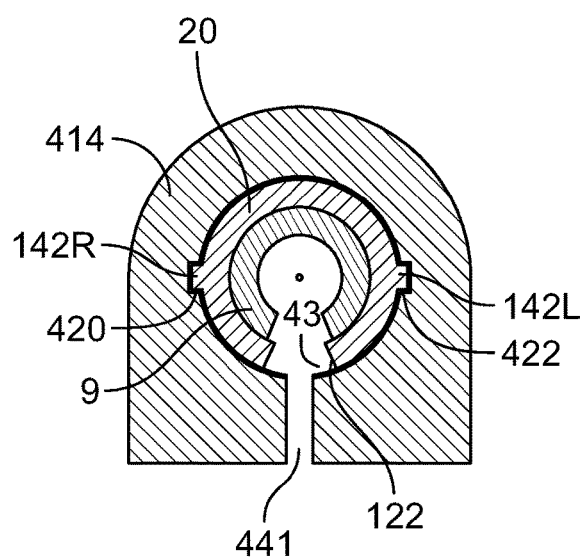

FIG. 40 is similar to FIG. 39. FIG. 40 shows the syringe 9, rotated 180° from FIG. 39, and thus oriented so that sheath 20's opening 43 coincides with the syringe 5's body front opening 122 of frame 9; and thus, needle assembly 14. is free to drop out of the socket 414, through socket bottom opening 441, and into the bottom 404 of the sharps container 400.

Figure 41:
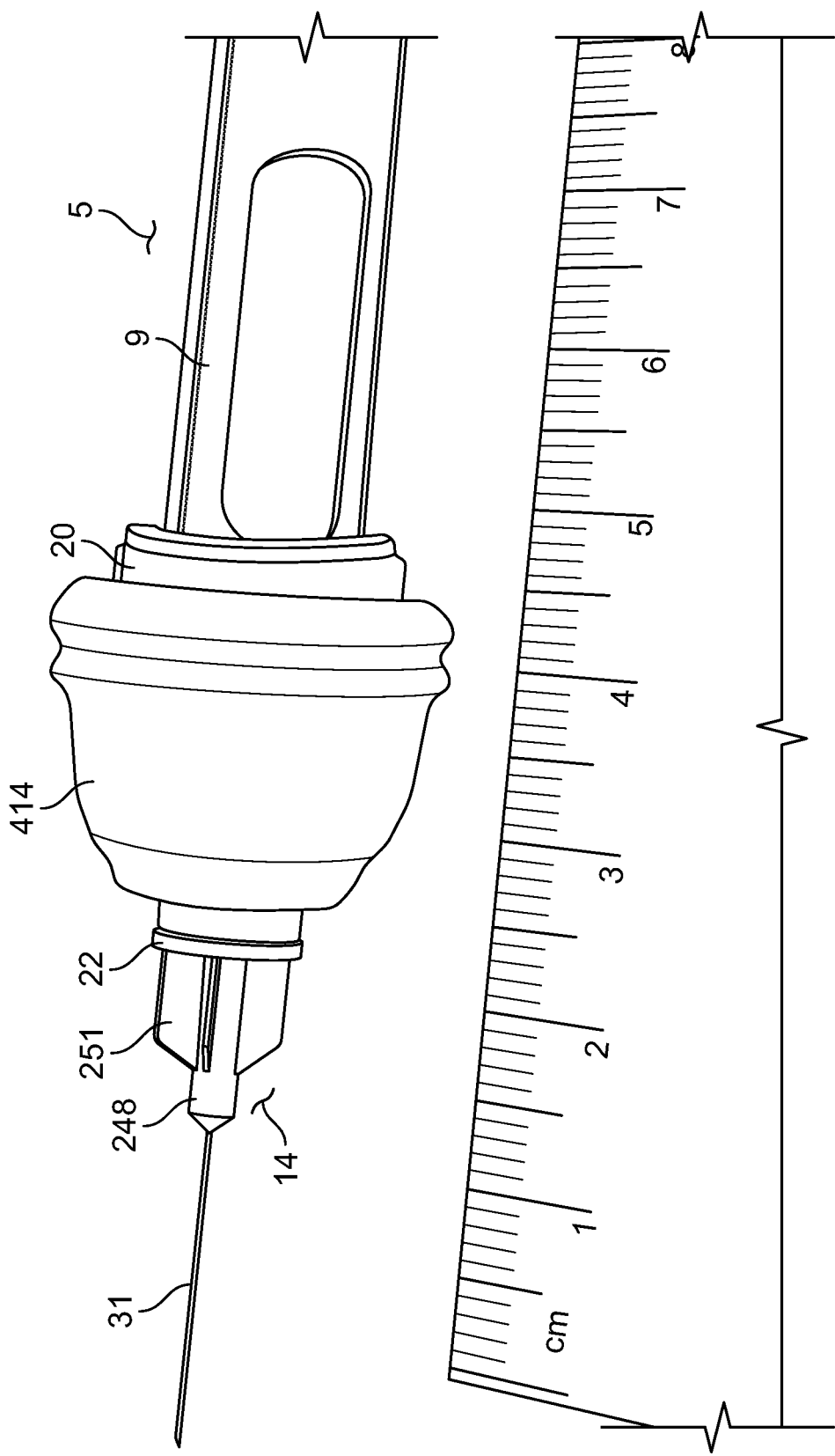
FIG. 41 is a top plan view of a socket.

FIG. 41 is a top plan view of socket 414 enclosing the sheath 20.

Figure 42:
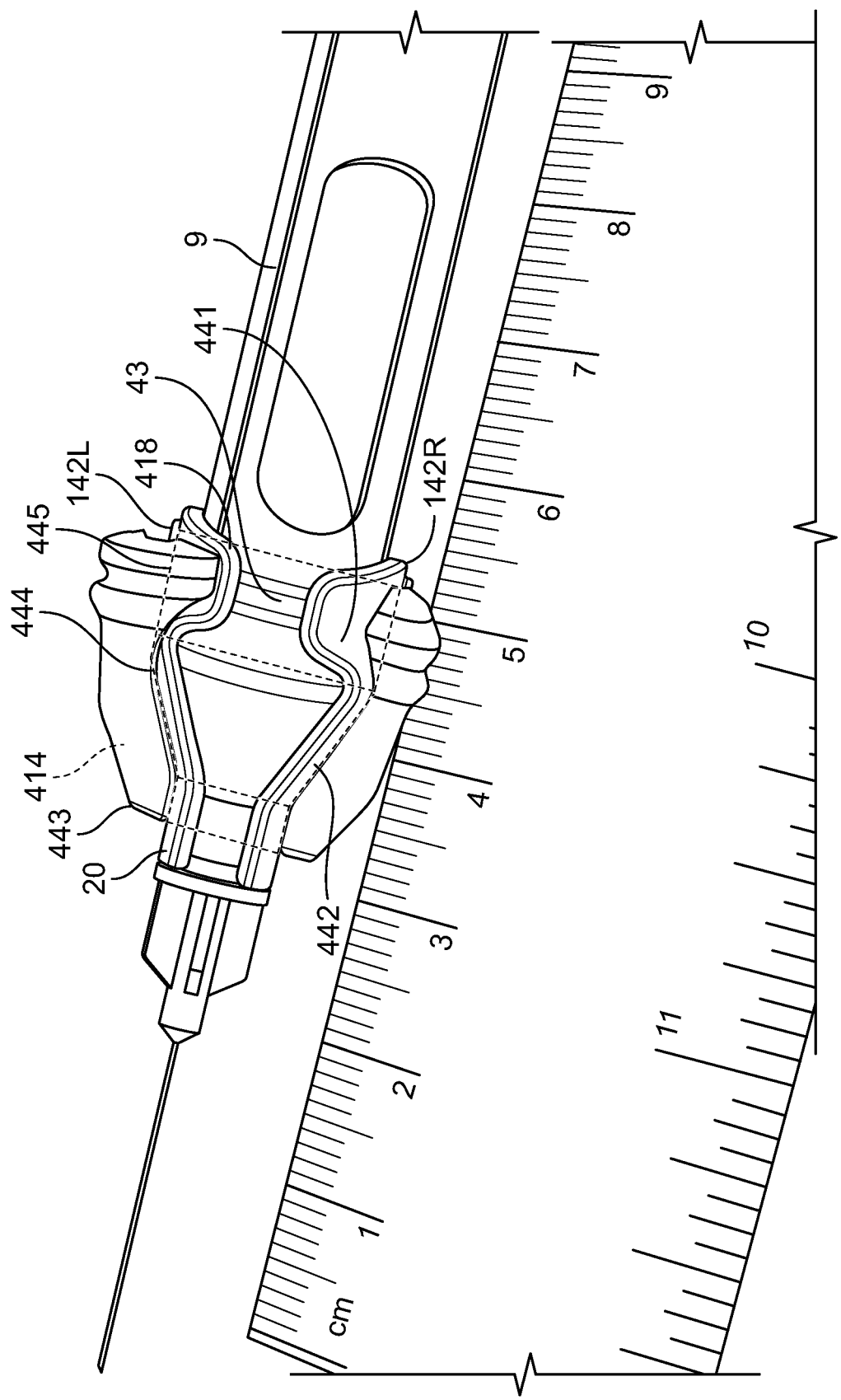
FIG. 42 is a bottom plan view of the socket with the syringe rotated closed.

FIG. 42 is a bottom plan view of socket 414, with socket bottom opening 441 aligned with the sheath opening 43. Syringe 9 is rotated closed, and thus needle assembly 14 is not free to drop out through the sheath opening 43, nor out of the socket 414, through socket bottom opening 441, and into the bottom 404 of the sharps container 400.

The sheath (20) is mounted rotatably to the syringe body (9). The sheath has a sheath gap (33) extending the length of the sheath, said sheath (20) having a sheath exterior surface 446, and a pair of ribs 142L and 142R protruding from the sheath exterior surface 446. Said ribs 142L and 142R are aligned in a direction parallel to the longitudinal axis 31A of the sheath 20, which axis coincides with the needle 31.

The socket (414) has a socket interior surface 442 which is selectively shaped to fit snugly and removably to the sheath exterior surface 446. The socket interior surface 442 has:
a tip-ward socket cylindrical segment 443,
a central socket conical segment 444, and
a ring-ward socket cylindrical segment 445;
all shown in dotted lines because the interior is hidden by intervening things.

The socket (414) comprises a socket bottom opening (441).

Said socket having a socket front opening (418).

Said front opening (418) is open to the socket interior surface (426).

The socket interior surface 442 comprises a longitudinal notch extended through the socket front opening (418) of the socket (414);

A pair of these longitudinal notches 420 & 422 are on the ring-ward socket cylindrical segment 445, of the socket interior surface 442. The longitudinal notches 420 & 422 are: aligned in a direction parallel to the longitudinal axis 31A of the socket 414, and placed so that the ribs 142L and 142R align with these longitudinal notches 420 & 422, and slide into said notches 420 & 422, when the needle assembly 14 is inserted through the socket front opening 418 of the socket 414, to fit snugly into the socket 414 interior surface 442. Said notches 420 & 422 hold the ribs 142L and 142R thereby keeping the sheath and socket aligned with socket bottom opening 441 aligned with the sheath opening 43 as syringe 5 is rotated.

Figure 43:
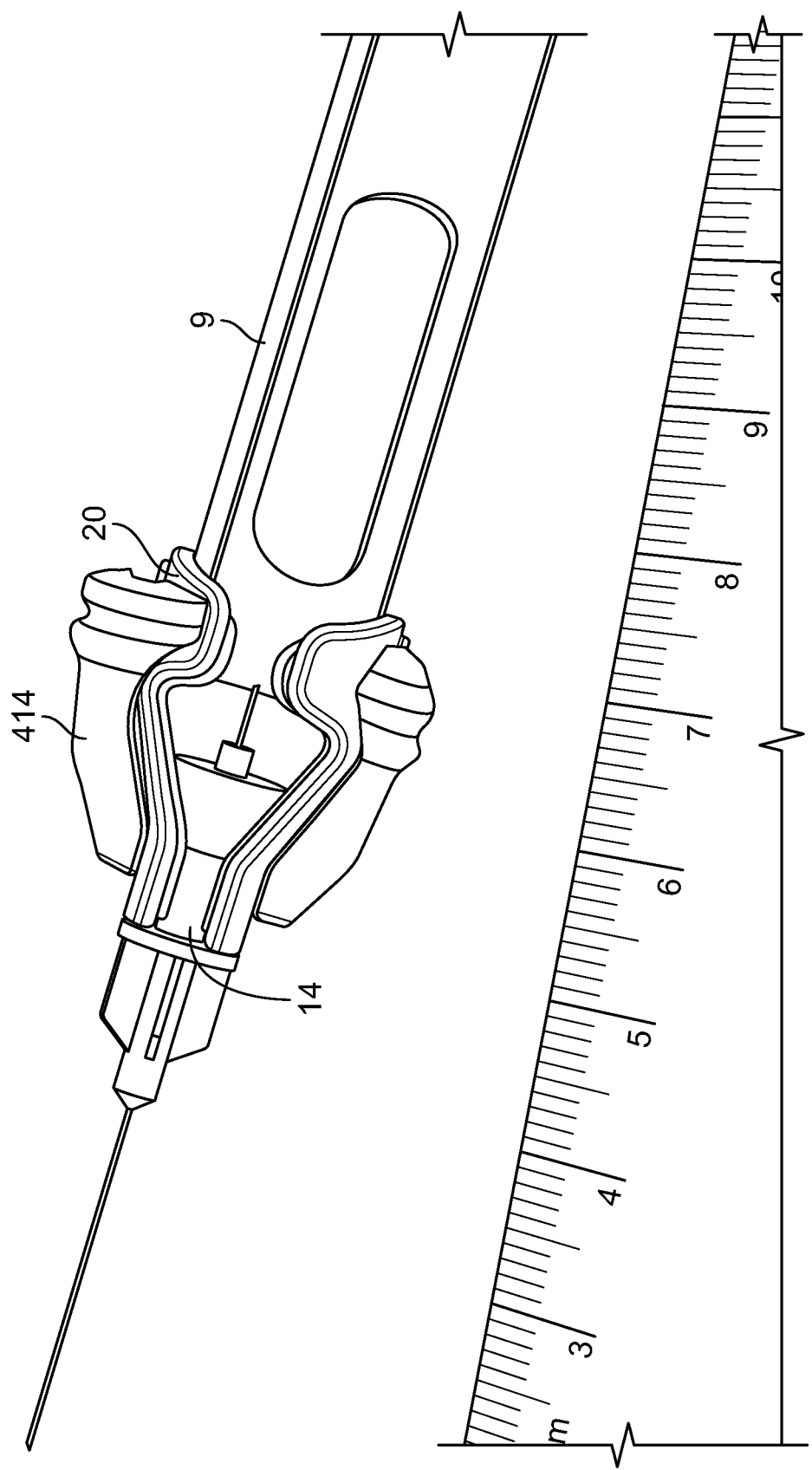
FIG. 43 is a bottom plan view of the socket with syringe rotated open.

When the syringe body 5 is rotated to the alignment depicted in FIG. 43: a bottom plan view of socket 414, with its socket bottom opening 441 aligned:
with the sheath opening 43 of sheath 20; and
with the front body opening 122 in the syringe body 9;
then, the needle assembly 14 drops down through the three aligned openings 122, 43, & 441, into the sharps container 400's bottom 404.

Figure 44:
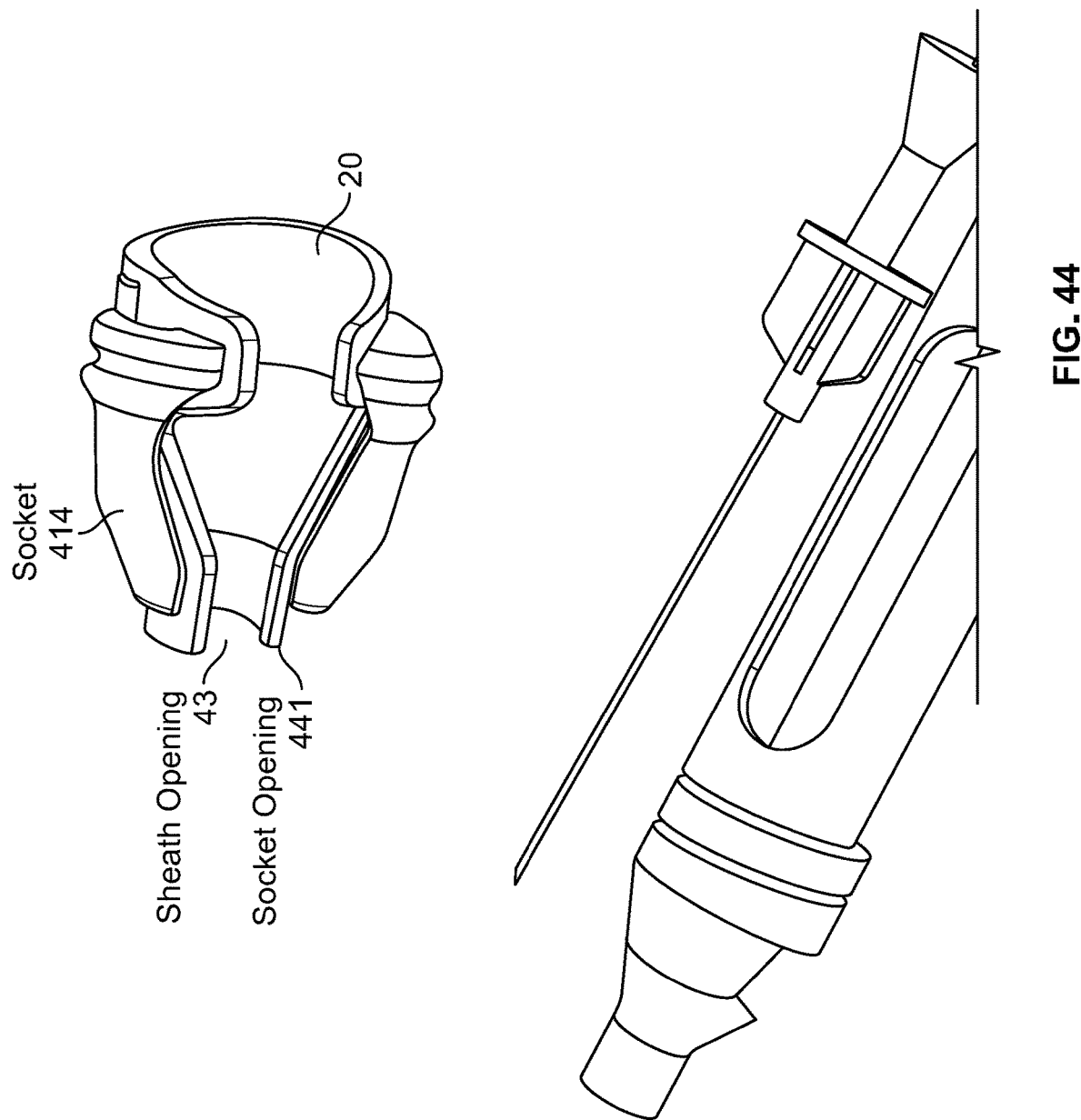
FIG. 44 is a perspective plan view of socket with the sheath rotated open.

FIG. 44 is a perspective plan view of socket 414 with socket bottom opening 441 and the sheath 20's sheath opening 43 aligned.

Alternate Needle Assembly Embodiment

Figure 45:
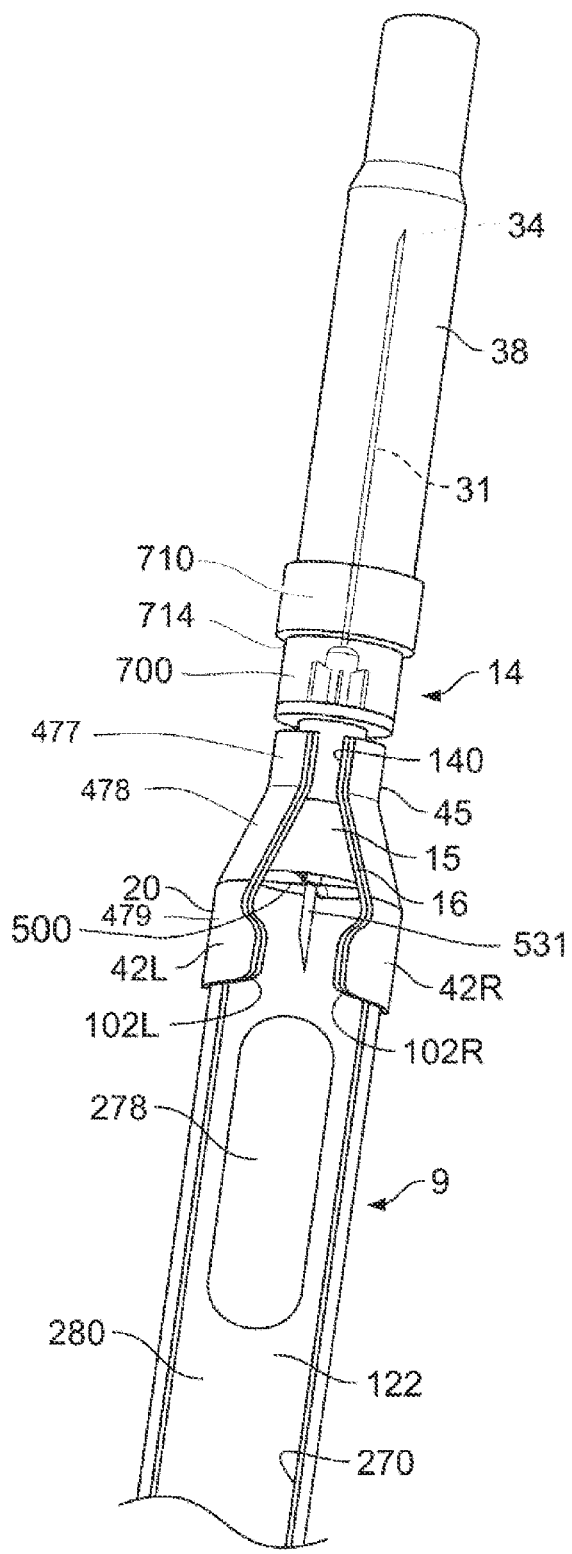
FIG. 45 is a perspective plan view of socket with the sheath rotated open to show an alternate embodiment of the needle assembly.

FIG. 45 is a perspective plan view of syringe 9 with the sheath 20 rotated open to show an alternate, non-self-aspirating embodiment of the needle assembly 14. The needle assembly 14 has a molded body 14B. At the ring-ward end of conical portion 15, the ring-ward surface of the cone is a molded surface from which the cartridge needle protrudes without the self-aspirating cylinder 240 shown in FIG. 6. Therefore, this embodiment does not assist in self-aspiration by the syringe. The dentist must manually retract the plunger with his thumb ring 7 (actuator ring 7).

Sheath 20 has: a tip-ward cylindrical section 477, section a central conical section 478, and a ringward conical section 479.

In FIG. 46, the needle assembly 14 has a molded body 14B. Cartridge needle 531 protrudes from a surface of the ringward end and must be the be manually aspirated.

Shown in FIGS. 47, 48, & 49, the needle assembly 14 has a ring-ward plane 500. Cone 15 is widest at its ring-ward end segment, widest part 631.

In FIGS. 48-49, a molded support comprises:
  plurality of four radial walls 501, radiate from a central molded core 504;
  which central molded core 504 ends tip-ward of the ring-ward plane 500.
  Inside conical portion 15 is a conical inner surface 502.
  Four radial walls 501, radiate from a central molded core 504.
  The radial walls 501 end at conical inner surface 502.
  The central molded core 504 surrounds needle shaft 14B.
  Each radial wall 501 has a top edge 507, which top edge 507 is below the ring-ward plane 500.
  Between the walls 501 are four interstitial spaces 511.
  Needle shaft 514 extends on the longitudinal axis 31A of the molded core 504 and then through the molded body 14B to the tip-ward end of the domed cylinder 248.

The ring-ward circumferential edge 510 of molded body 14B is at ring-ward plane 500.

The ring-ward circumferential edge 510 is annular in shape, and has at its widest part 631 an outer diameter 631 of 7.1 mm and an inner diameter of 6.1 mm, giving a wall thickness of 0.5 mm.

A standard dental medicine cartridge 12 has an endcap 303 (FIG. 50) having an end surface 622 with an outer diameter 622 of 7.9 mm, and a diaphragm opening 622 of 3.5 mm in diameter, which exposes a diaphragm 301.

To install the needle assembly 14 into the syringe, conical part 15 of needle assembly 14 has been firmly located against the cone inside 140 of syringe cone 16, by the pressure of tip-ward surface 107 (FIG. 4) of sheath 20. Harpoon 11 has forced plunger 22 and cartridge 12 inside the syringe body 5, towards the ringward end of 500 of the needle body 14B, and the cartridge needle 531 has penetrated the center of diaphragm 301, with the cartridge 12 coaxial to the needle assembly 14.

Then the larger 7.9 mm diameter 630 abuts and covers the smaller 7.1 mm outer diameter of 631 of ringward edge 510. This abutment thus supports the cartridge 12, under tip-ward pressure of actuator ring 7 through the plunger (7, 10, 11, 13).

In manufacturing the needle 14A to molded body 14B, a glue, such as epoxy, is applied to the outside of a tip-ward part (31) hereinafter tip-ward needle (31) of needle 14A, where the tip-ward needle 31 is to be placed inside the tip ward end within domed cylinder 248 of molded body 14B, within needle shaft 514 of molded body 14B. Thus, when the needle 31 is inserted into needle shaft 514, and it has reached its intended axial location, then the needle is held in position until the glue sets, and the glue holds the needle affixed to the shaft within domed cylinder 248. The tip-ward needle 31 becomes affixed inside molded body 14 at domed cylinder 248.

But at the other (ring-ward) end of needle 14B, the ringward cartridge needle 531 fits loosely in inside needle shaft 514. The shaft 514 passes through the center of rib core 504 at the ringward end of cone 15 (FIGS. 48-49).

Unlike FIGS. 6 & 20A, self-aspirating cylinder 240 is absent from FIGS. 45-49; so that the absent cylinder 240 does not reinforce the cartridge needle 231 of needle assembly 14 at its ringward (cartridge-ward) end as it does in FIG. 6.

The inventor prefers to use a 27-gage needle 31, because his experience has shown the patients experience less pain than with a larger gage needle such as a 25 gage. The use of medicine cartridges allows use of a smaller gage needle, than would be optimum if medication needed to be drawn into the syringe via the needle 31.

Harpoon 11 (FIG. 1) must be inserted and anchored to slidable seal 13 in the ringward end of medicine cartridge 12, mounted in syringe body 9 of syringe 5. Medicine cartridge 12 has a slidable seal 13, into which harpoon 11 forms a plunger (13, 11, 10, & 7) with shaft 10, which can then be slid either:
  tip-ward; or
  ring-ward;
  by manipulating the actuator ring 7 in those directions.

The actuator ring 7 is thus configured to be controlled by the dentist's or a user's 430 thumb, controlling the actuator ring 7 to expand or contract the volume of the cartridge.

The dentist retracts the syringe plunger after the initial stick, in order to ascertain that the point at tip 34 or 311 is not within a blood vessel, by:
  using his thumb in the thumb ring of the syringe,
  pulling ringward on the plunger to lower the air pressure within the cartridge, and
  observing the anesthetic vial to determine if red blood has been pulled into the syringe cartridge.

If red blood has been pulled into the cartridge 12, the red visible within the cartridge cylinder 12 indicates that the dentist must find a new spot for the injection point, in order to avoid injecting anesthetic into the bloodstream via a blood vessel.

FIG. 46 is an exploded perspective view of the alternate embodiment of the needle assembly 14, with protective caps 38 and 238 vertically exploded to show the medicine-vial-penetrating needle 531.

The needle assembly includes ringward plane 500 of the needle assembly 14.

Unlike in FIGS. 6 & 20A, self-aspirating cylinder 240:
  is absent from FIGS. 45-47, and therefore:
  does not protrude onto the cartridge diaphragm to create a self-aspirating feature, nor
  reinforce the cartridge needle 231 of needle assembly 14 at its ring-ward (cartridge-ward) end 500, 510.

Therefore, there is no self-aspirating effect when pressure on the actuator ring is merely relaxed.

Therefore, the harpoon 11 (FIG. 1) must be deliberately withdrawn ringward, to reduce atmospheric pressure within the cartridge, and, if the needle 31's tip 34 or 311 is in a blood vessel, suck back some red blood into the cartridge 12, thus the red blood within the cartridge warning the dentist:
  that tip 311 is in a blood vessel, and
  tip 311 must be relocated before injecting anesthetic.

The needle assembly 14, without the self-aspirating cylinder 240 (FIG. 6) will also be:
  easier, faster, and less expensive to manufacture, when molding the molded body 14B, than
  molding the molded body 14B embodiments of FIGS. 6 and 20A.

Figure 47A:
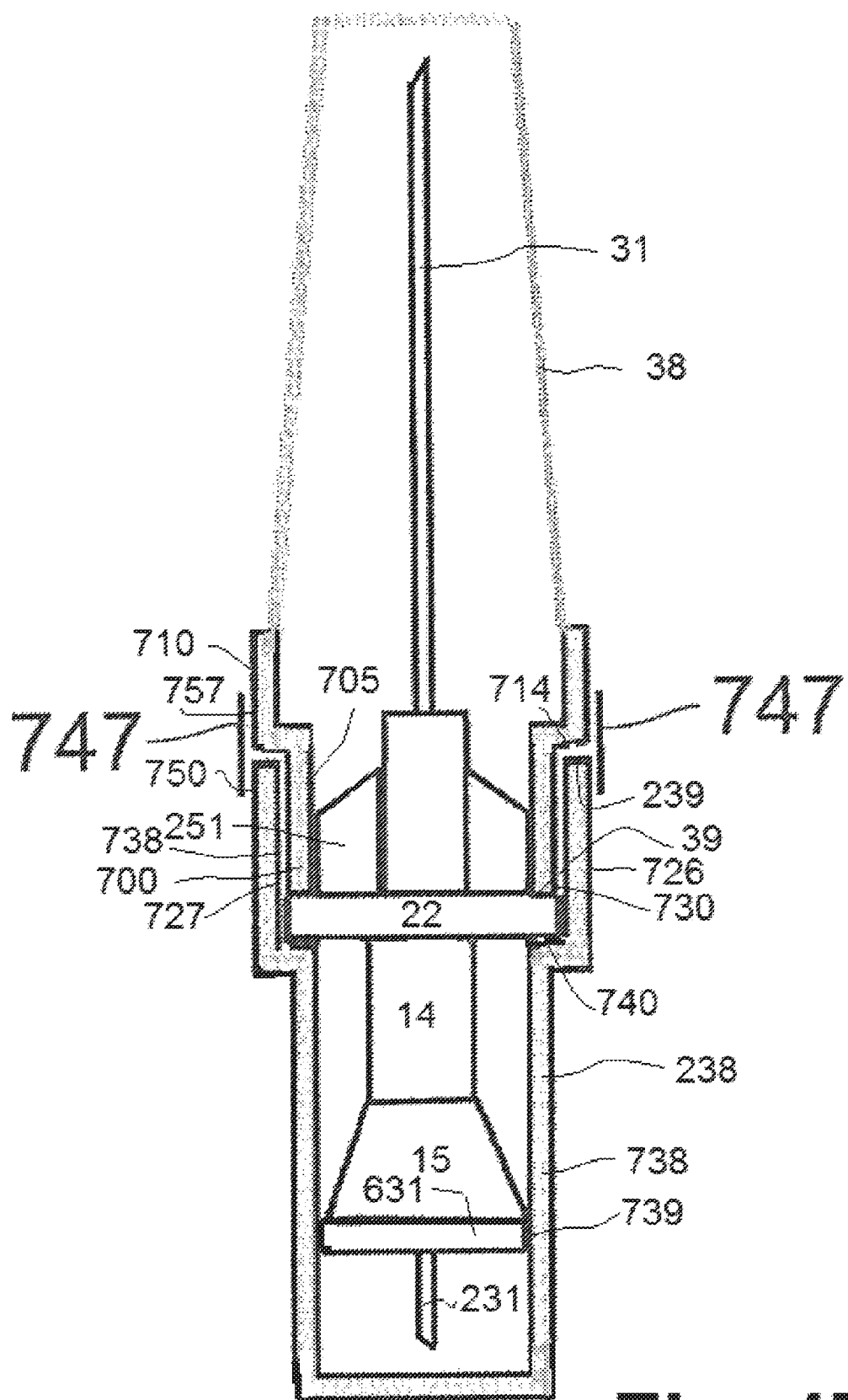
FIG. 47A is an elevation, partially in section through the center of the protective caps, but showing the outside surface of the needle assembly.

FIG. 47A is an elevation, partially in section through the center of the protective caps 38 & 238, but showing the outside surface of the needle assembly 14.

The needle assembly 14 is sterilized and assembled with the sterile protective caps 38 & 238. Protective cap 38 protects needle 31, to prevent needle 31 from stabbing a user accidentally.

Cartridge protective cap 238 protects cartridge needle 231, to prevent cartridge needle 231 from stabbing a user accidentally.

The protective cap 38 has a ring-ward edge 39. Ring-ward edge 39 abuts needle flange 22.

The protective cap 38 has a ring-ward cylindrical cap segment 700. The ring-ward cylindrical cap 38 segment 700 has an inside surface 705, sized to friction-fit the outer radius of fins 251.

The protective cap 38 has a center cylindrical cap segment 710 larger than the ring-ward cylindrical cap segment 700. The center cylindrical cap segment 710 forms an annular shoulder 714, against which a cartridge needle cap tip-ward edge 239, of the cartridge needle protective cap 238 abuts.

Cartridge needle protective cap 238 has a tip-ward cylindrical segment 726.

Tip-ward cylindrical segment 726 has an inner surface 727 which is friction-fit to an outer surface 730 of tip-ward cylindrical segment 726, to hold cartridge needle protective cap 238 in place.

Ring-ward cartridge needle protective cap segment 738 is narrower than tip-ward cylindrical segment 726, so that the inner surfaces form a cartridge needle protective cap shoulder 740. Cartridge needle protective cap shoulder 740 abuts needle assembly flange 22 to stabilize the cartridge needle protective cap 238.

Cartridge needle protective cap 238's tip-ward cylindrical segment 726 has an inner surface 738.

Cartridge needle protective cap's 238 ring-ward cylindrical segment 738's inner surface 739 is a friction fit with ring-ward end segment widest part 631 of needle assembly 14.

Figure 47B:
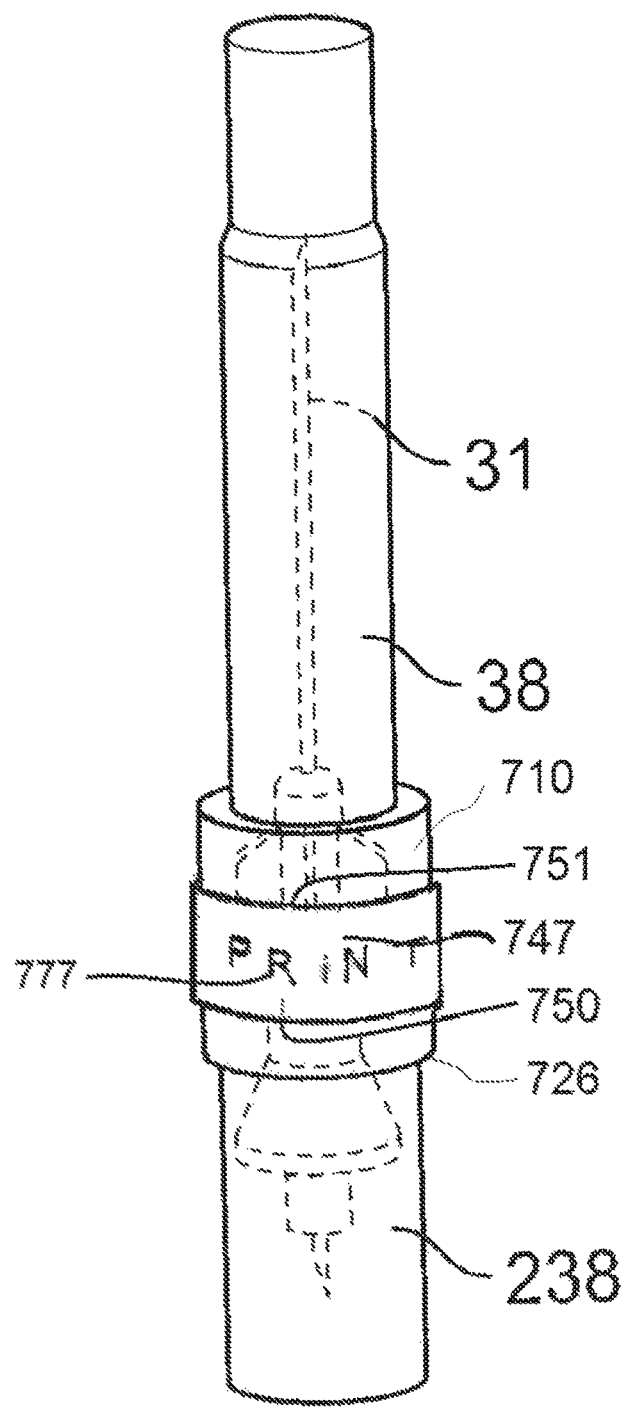
FIG. 47B is an oblique view of the protective caps, but showing the outside surface of the needle assembly.

FIGS. 47A & 47B show a tamper-evident protective strip of paper 747 is adhesively wrapped around an outer surface 757 of center cylindrical cap segment 710, where surface 757 is adjacent to an outer surface 750 of tip-ward cartridge needle protective cap segment 726. The strip of paper 747 is adhesively wrapped around both adjacent outer surfaces 757 and 750, so that when the cartridge needle protective cap 238 is removed, the strip of paper 747 is torn, to indicate loss of sterility, and discourage later use or inadvertent re-use of needle assembly 14, even if the protective caps have been replaced.

The strip of paper 747 is distinctively printed 777 to facilitate authentication, and to provide a further visual indicator of past use, because the torn-in-two printed halves of the paper strip are unlikely to match up if the caps are replaced simply to protect against needle sticks from within the trash bags.

The printed strip 747 is seen in the photo that comprised informal FIG. 20, and a torn piece of a printed strip 747 is seen in the photo that comprised informal FIG. 1; of this application's priority U.S. Provisional Patent Application 62/118,310, filed 19 Feb. 2015, and which has been incorporated by reference in all the subsequent applications.

I claim:

1. A needle assembly, for use with a syringe and a medicine cartridge; said needle assembly comprising:
  a molded body;
  a needle housed in, affixed to, and reinforced by the molded body;
  said needle comprising a single tube which tube comprises:
    a tip,
    a tip-ward needle extending ring-ward from said tip into the molded body;
    said tip-ward needle becoming a cartridge needle within the molded body;
    said cartridge needle extending tip-ward from the molded body;
  said molded body, molded as a single structure, and comprising:
    a domed cylinder, at the molded body tip-ward end;
    a flange ringward of said molded body;
    a plurality of fins, said fins molded radially from the domed cylinder, and said fins vertically molded from said flange; and reinforcing said fins to said flange;
    a second cylinder, molded extended ringward from said flange;
    a conical portion molded ringward from said second cylinder, said cone flaring out ring-ward to a widest part of the conical portion, at a ringward end of said molded body;
    an annular surface at the widest part of the conical portion;
    said cartridge needle having a molded support located tip-ward of the annular surface;
    a needle shaft, said needle shaft at a central longitudinal axis of said molded body;
    said needle passing through needle shaft;
  wherein the molded support comprises:
    a central molded core;
    a plurality of radial walls, radiating from the central molded core;
    the central molded core ends tip-ward of the ring-ward end;
    inside of the conical portion is a conical inner surface;
    the radial walls end at the conical inner surface;
    the central molded core surrounds the needle shaft;
    each radial wall has a top edge, which top edge is below the ring-ward plane; and
    between the radial walls are a plurality of interstitial spaces.

2. The needle assembly, according to claim 1, further comprising:
  a protective cap protecting the tip-ward needle;
  a cartridge needle protective cap protecting the cartridge needle;
  the protective cap having a ring-ward edge;
  the cartridge needle protective cap having a tip-ward edge;
  the needle protective caps abut each other at their respective edges;
  a tamper-evident protective strip of paper is adhesively wrapped around both protective caps.

3. The needle assembly, according to claim 1, in which:
  the annular surface has measurements, at the widest part:
    an outer diameter of 7.1 mm and the annular surface has an inner diameter of 6.1 mm., giving a wall thickness of 0.5 mm;

the annular surface's measurements would be coincident with a standard dental medicine cartridge endcap, said endcap having an end surface with an outer diameter of 7.9 mm, and a diaphragm opening of 3.5 mm in diameter; when the annular surface and the end surface are aligned coaxially within a syringe body.

4. A needle assembly, for use with a syringe and a medicine cartridge; said needle assembly comprising:
a molded body;
a needle housed in, affixed to, and reinforced by the molded body;
said needle comprising a single tube which tube comprises:
a tip,
a tip-ward needle extending ring-ward from said tip into the molded body;
said tip-ward needle becoming a cartridge needle within the molded body;
said cartridge needle extending tip-ward from the molded body;
said molded body, molded as a single structure, and comprising:
a domed cylinder, at the molded body tip-ward end;
a flange ringward of said molded body;
a plurality of fins, said fins molded radially from the domed cylinder, and said fins vertically molded from said flange; and reinforcing said fins to said flange;
a second cylinder, molded extended ringward from said flange;
a conical portion molded ringward from said second cylinder, said cone flaring out ring-ward to a widest part of the conical portion, at a ringward end of said molded body;
an annular surface at the widest part of the conical portion;
said cartridge needle having a molded support located tip-ward of the annular surface;
a needle shaft, said needle shaft at a central longitudinal axis of said molded body;
said needle passing through needle shaft;
wherein the needle system is used in a cartridge syringe system comprising:
a syringe;
said syringe having the tip-ward direction and the ring-ward direction;
the syringe comprises:
a syringe body;
an actuator ring;
a shaft slidably mounts the actuator ring to the syringe body;
a harpoon at a tip-ward end of the shaft;
the syringe body comprises a spiral body mount external to the syringe body configured to removably mount a sheath rotatably to the syringe body;
said sheath has an internal spiral mount configured to removably mount the sheath rotatably to the spiral body mount external to the syringe body;
said sheath has a front sheath opening;
the syringe body has a body front;
the body front has a body front opening;
the front sheath opening and the body front opening are configured of cooperatively similar size and shape so that the front sheath opening is rotatable to:
an open position, where the front sheath opening and the body front opening coincide, to permit installation of a needle assembly into the syringe body or removal of the needle assembly from the syringe body; or
a closed position, where the front sheath opening and the body front opening do not coincide, and thereby retain the needle assembly in the syringe body;
in which cartridge syringe system:
said internal spiral mount spiral is an internal thread;
said spiral body mount is an external groove;
said internal thread is configured to rotatably mate with the external groove thereby, rotatably mounting the sheath to the syringe body, mounting to the external groove on the outside of the syringe body;
the sheath comprises:
a left sheath tab; and
a right sheath tab;
extending into the front sheath opening;
a pair of front wall tabs, comprising:
a left front wall tab, and
a right front wall tab,
extending from the syringe body into said front body opening;
the left front wall tab is spaced from the right front wall tab by a gap; and
in the closed position, one of the sheath tabs closes the gap.

5. The cartridge syringe system according to claim 4, further comprises:
said front body opening has a plurality of varying front body opening widths;
the sheath opening has a plurality of the varying sheath opening widths;
the varying sheath opening widths are configured to be rotatable, to coincide with the varying front body opening widths, to thereby open the front body opening; and
the varying sheath opening widths are configured to be rotatable, to not coincide with the varying front body opening widths, and thereby to close the front body opening;
the syringe body has an inside of a syringe cone;
having a tip-ward body opening width of the varying front body opening widths;
the tip-ward body opening width configured to:
allow the tube reinforcement to pass through the tip-ward body opening width and the tip-ward sheath opening width when the tip-ward body opening width and the tip-ward sheath opening width are coincided; and
retain the tube reinforcement when said the tip-ward body opening width and the tip-ward sheath opening width are not coincided.

6. The cartridge syringe system according to claim 5, in which, rotating the sheath from the seated position:
I. unseats the needle assembly from the syringe body;
II. coincides the sheath opening widths with the varying front body opening widths and thereby opens the body front opening; and
III. allows the tube reinforcement to pass through a tip-ward body opening width and the tip-ward sheath opening width when coincided;
for disposal of the needle assembly from the body.

7. The cartridge syringe system according to claim 5, in which the sheath has:
an outer circumference; and
a grip rib on said outer circumference.

8. The cartridge syringe system according to claim 7, in which the sheath has an opposite grip rib on an opposite side of said outer circumference.

9. The cartridge syringe system according to claim 7, including:

a sharps socket;
the sharps socket has a front opening;
a left notch and a right notch in the opening of the sharps socket are configured to engage the finger ribs, on the outside of the sheath,
the socket has an interior surface configured to closely receive and frictionally engage an outer surface of the sheath;
the needle assembly is held in place by the sheath;
the screw threads hold the flange, by the sheath's pressure against the flange, as in figure;
the front of the sheath is closed at gaps, to prevent the needle assembly from escaping the front body opening in the syringe body.

10. A method of using a cartridge syringe system, said cartridge syringe system including:
a sheath;
said sheath having an internal sheath thread, spiraling inside the sheath;
a syringe body having an external body thread configured to screw to the internal sheath thread;
a needle assembly;
said needle assembly comprising a molded reinforcement;
said method comprising the steps of:
placing the sheath coaxially tip-ward of the syringe body;
pushing the sheath ring-ward onto the syringe body;
thereby:
deforming the sheath open, to engage the internal sheath thread to the external body thread; and
to thereby secure the sheath to the syringe body;
aligning an opening in the sheath to a similarly configured opening in the syringe body;
Inserting the molded reinforcement of the needle assembly through:
said aligned opening in the sheath, and
the opening in the syringe body;
rotating said aligned opening in the sheath out of alignment to the opening in the syringe body, to:
thereby retain the needle assembly to the syringe body; and
drive a flange of the needle assembly tip-ward; and
thereby seat a conical part of the needle assembly against a conical end of syringe body;
inserting a diaphragm of a medicine cartridge through a cartridge opening into a compartment in the syringe body;
impaling the diaphragm of the medicine cartridge onto a ring-ward point of the needle;
seating a remainder of the medicine cartridge in the syringe body;
moving an actuator ring tip-ward;
thereby moving a shaft, with a harpoon on an end of the shaft tip-ward towards the medicine cartridge;
thereby impaling a sliding seal in the medicine cartridge with the harpoon on the shaft, to form a plunger;
driving the plunger tip-ward to fill the needle with a medicine;
penetrating a target with the needle;
withdrawing the plunger, to test whether a tip of the needle is adversely located in blood vessel; by observing the cartridge and:
a. if the cartridge has no red color in the medicine, then
b. injecting the medicine from the medicine cartridge into the target.

11. The method of using a cartridge syringe system according to claim 10, said method comprising the further steps:
c. if the medicine in the cartridge in shows red coloration, then:
d relocating the tip, and
e. withdrawing the plunger, to test whether the tip of the needle is adversely located in blood vessel;
f. if the color in the medicine has not become redder, then: injecting the medicine from the medicine cartridge into the target; but
g. if the medicine in the cartridge shows increased red coloration, then: repeating the above steps d through g until the color in the medicine has not become redder, then:
f. injecting the medicine from the medicine cartridge into the target.

12. The method of using a cartridge syringe system, according to claim 11, said method including the further steps of:
withdrawing the actuator ringward; thereby withdrawing the harpoon from the medicine cartridge;
aligning the opening in the sheath to the similarly configured opening in the syringe body; and
grasping the medicine cartridge;
pushing the medicine cartridge ringward to dislodge the diaphragm from the cartridge needle;
pushing the medicine cartridge from a cartridge ejection slot in the syringe body to eject the medicine cartridge through a front opening in the syringe body.

13. The method of using a cartridge syringe system, according to claim 12, said method including the further steps of:
inserting a diaphragm of a new medicine cartridge which new medicine cartridge is full, through a cartridge opening into a compartment in the syringe body;
impaling a diaphragm of the new medicine cartridge onto a ring-ward point of the needle;
seating a remainder of the new medicine cartridge in the body;
moving the actuator ring needle-ward;
thereby moving a shaft, with a harpoon on an end of the shaft towards the medicine cartridge;
thereby impaling the sliding seal in the medicine cartridge with the harpoon on the shaft, to again form the plunger;
driving the plunger tip-ward to fill the needle with a medicine;
penetrating a target with the needle; and
then injecting the medicine from the medicine cartridge into the target;
repeating until a procedure is done, and there is no further need to administer more medication;
aligning the opening in the sheath to the similarly configured opening in the syringe body;
ejecting the molded reinforcement of the needle assembly:
through said aligned opening in the sheath, and
through the opening in the syringe body; and
into a sharps container.

14. The method of using a cartridge syringe system, according to claim 13, said method including the de-tipping steps of:
orienting the sheath so that the gap is facing down;
directing the tip of the needle towards a socket in a surface of a sharps container;
when the tip is inside an opening, then the needle, the needle assembly, and the sheath help guide the sheath into the socket;
inserting rib into notch in sharps socket;

rotating the syringe thereby relieving a pressure on flange of the needle assembly;

ending rotating when the syringe has been rotated 180° from the syringe's original position, so that an opening is now beneath the syringe and opening is aligned with the opening in the sheath;

thereby allowing the needle assembly to fall through the gaps of syringe, and through the sheath, through the socket, into the bottom of the sharps container;

withdrawing the syringe from the sharps socket.

15. The method of using a cartridge syringe system, according to claim 13, in which the rotating of the syringe is clockwise, thereby relieving a pressure on the flange of the needle assembly.

16. The method of using a cartridge syringe system, according to claim 13, in which the rotating of the syringe is counterclockwise, thereby relieving a pressure on the flange of the needle assembly.

\* \* \* \* \*